(12) United States Patent
Briesewitz et al.

(10) Patent No.: US 9,260,484 B2
(45) Date of Patent: Feb. 16, 2016

(54) SMALL MOLECULE COMPOSITE SURFACES AS INHIBITORS OF PROTEIN-PROTEIN INTERACTIONS

(75) Inventors: Roger Briesewitz, Columbus, OH (US); Dehua Pei, Columbus, OH (US); Xianghong Wu, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/126,343

(22) PCT Filed: Jun. 15, 2012

(86) PCT No.: PCT/US2012/042827
§ 371 (c)(1),
(2), (4) Date: Mar. 27, 2014

(87) PCT Pub. No.: WO2012/174489
PCT Pub. Date: Dec. 20, 2012

(65) Prior Publication Data
US 2014/0200186 A1    Jul. 17, 2014

Related U.S. Application Data

(60) Provisional application No. 61/497,393, filed on Jun. 15, 2011.

(51) Int. Cl.
A61K 38/00    (2006.01)
A61K 38/12    (2006.01)
C07K 11/02    (2006.01)

(52) U.S. Cl.
CPC ............... *C07K 11/02* (2013.01); *A61K 38/12* (2013.01)

(58) Field of Classification Search
None
See application file for complete search history.

(56) References Cited

U.S. PATENT DOCUMENTS 6,921,531 B2 * 7/2005 Briesewitz et al. .......... 424/94.5
7,390,784 B2 * 6/2008 Briesewitz et al. ............ 514/1.3
2013/0164317 A1   6/2013 Yousef et al.

FOREIGN PATENT DOCUMENTS

WO    WO-2005/009457    2/2005
WO    WO-2010/101622    9/2010
WO    WO-2012/174489    12/2012

OTHER PUBLICATIONS

Dhanasekaran et al, Scaffold proteins of MAP-kinase modules (Oncogene (2007) 26, 3185-3202).*
Moro et al, Constitutive activation of MAPK/ERK inhibits prostate cancer cell proliferation through upregulation of BRCA2 (International Journal of Oncology 30: 217-224, 2007).*
Chabard et al, ERK implication in cell cycle regulation (Biochimica et Biophysica Acta 1773 (2007) 1299-1310).*
International Search Report and Written Opinion for PCT International Application No. PCT/US2012/042827, mailed Nov. 30, 2012, 10 pages.
Tamaki et al. (2011), "Novel gratisin derivatives with high antimicrobial activity and low hemolytic activity", Bioorganic & Medicinal Chemistry Letters, 21(1): 440-443.
Upadhyaya P. et al. (2015), "Inhibition of Ras Signaling by Blocking Ras-Effector Interactions With Cyclic Peptides", Angewandte Chemie International Edition, May 7, 2015, vol. 127, pp. 7712-7716.
Villalona-Calero (2010), "Challenging Targets in Lung Cancer", Lung Cancer Conference, Power Point presentation, The Ohio State University, 50 pages.
Wu X. et al. (2013), "Inhibition of Ras-Effector Interaction by Cyclic Peptides", MedChemComm, Feb. 1, 2013, vol. 4, No. 1, pp. 378-382.

* cited by examiner

*Primary Examiner* — Karlheinz R Skowronek
*Assistant Examiner* — Sergio Coffa
(74) *Attorney, Agent, or Firm* — Foley & Lardner LLP; Antoinette F. Konski; Lydia B. Choi

(57) ABSTRACT

A method of inhibiting a binding event between a target protein and a binding protein, comprising administering to a cell in vitro an effective amount of a non-naturally occurring bifunctional inhibitor molecule including (a) protein binding moiety, and (b) an effector region, wherein the protein binding moiety binds to a blocking protein, and wherein the effector region binds to the target protein in order to bind the target protein and the blocking protein and prevent access of the binding protein to the target protein. This abstract is intended as a scanning tool for purposes of searching in the particular art and is not intended to be limiting of the present invention.

9 Claims, 14 Drawing Sheets

SMALL MOLECULE COMPOSITE SURFACES AS INHIBITORS OF PROTEIN-PROTEIN INTERACTIONS

CROSS-REFERENCE TO RELATED APPLICATIONS

This Application is a national phase application of International Application No. PCT/US2012/042827, filed Jun. 15, 2012, which claims the benefit of U.S. Provisional Application No. 61/497,393, filed on Jun. 15, 2011; which are incorporated herein by reference in entirety.

STATEMENT REGARDING FEDERALLY SPONSORED RESEARCH OR DEVELOPMENT

This invention was made with government support under Grant Agreement Nos. GM062820; AI62901, and CA132855, awarded by the National Institutes of Health. The United States government has certain rights in the invention.

BACKGROUND

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

The inhibition or activation of biological processes with drugs that act as antagonists or agonists is the basis of the chemotherapy of diseases. For a small molecule to interact with high affinity and specificity with a given protein target requires that the molecule is able to establish a sufficient number of molecular interactions which will provide the required free energy of binding. If the active site of a protein is a deep pocket, small molecule drugs can take advantage of interactions that can be established on all sides of the molecule. However, if the active site of a protein target is relatively flat, the contacts a small molecule can establish may be limited to one face. As a result, the affinity of the small molecule for the target may not be very high.

Protein-protein interactions (PPIs) occur when two or more proteins bind together, and they represent a large group of drug targets. However, PPIs are difficult to disrupt because they usually involve large, two-dimensional (i.e., flat) target surfaces. The interface of protein-protein interactions can be rather large and may involve contacts between 20 or 30 amino acids on both proteins. Conventional small molecule drugs can bind with high affinity in deep protein pockets that provide a three-dimensional building space. However, due to the flat surface of many PPI's, small molecules often cannot establish the number of contacts required for a high affinity binding event that can compete with the binding of the large protein ligand to the target. Thus, most PPIs are "undruggable" with traditional small molecules, which is a problem.

The development of small molecules that can inhibit PPIs could have great benefit. For example, K-Ras is a member of the small GTP binding protein family which constitutes over 100 members[10]. Wild-type K-Ras oscillates between an active, GTP-bound form and an inactive GDP form[11,12]. The GTP-bound form has a distinct conformation that promotes its interaction with multiple effector proteins via its Switch I and Switch II regions. 30% of all solid tumors show activating point mutations in K-Ras. K-Ras mutants are insensitive to down regulation by GAP-mediated hydrolysis of bound GTP. As a result, mutant K-Ras is "frozen" in its activated form which results in constitutive signaling into proliferation and survival pathways. K-Ras point mutations are usually found at codons 12, 13 and 61 and less frequently at codons 59 and 63. Typical point mutations at codon 12 replace a glycine by aspartate or valine. Transgenic mouse models have demonstrated that expression of mutated K-Ras by itself[13] or in combination with the introduction of other oncogenic lesions[14,15] can promote cancer. Similarly, it was shown that cancer cells undergo apoptosis if oncogenic K-Ras is down regulated by RNA interference.[16] These data strongly suggest that inhibition of oncogenic K-Ras may have therapeutic benefits in cancer patients. K-Ras is farnesylated and located at the inner leaflet of the plasma membrane. In recent years the pharmaceutical industry has attempted to target oncogenic K-Ras proteins by disrupting its subcellular localization with farnesyl transferase inhibitors (FTIs). However, in clinical trials FTIs have proved largely ineffective in pancreatic and other cancers, possibly because the loss of FT activity is compensated for by geranyl-geranyl transferase[17].

In view of the above issues, there have been previous attempts develop approaches to modulate the biological activity of small molecules. For example, prior studies have demonstrated that the affinity of a linear peptide for the Fyn SH2 domain can be enhanced when the peptide is coupled to an FKBP ligand and bound to FKBP.[47]

As another example, it has been shown that conjugation of an FKBP ligand to Congo Red, a dye molecule that binds to beta-amyloid peptide, improved the ability of the dye molecule to disrupt amyloid plaque formation.[48] Presumably, binding of FKBP to the molecule creates a steric block FKBP that hinders the beta-amyloid peptide aggregation.

As yet another example, it has been shown that linking a HIV protease inhibitor to an FKBP ligand increased the half-life of the drug in mice.[49] It was thought that the association of the bifunctional molecule with FKBP in mammalian cells may have slowed the molecule's metabolism and excretion.

However, a drawback to these previous studies is that they all required a pre-existing ligand with high affinity and specificity to the target of interest. Unfortunately, for many high-value targets such as the flat surfaces involved in protein-protein interactions, no such ligand is available (or possible).

As such, the development of a technique that would allow the disruption of protein-protein interactions, particularly through use of a small molecule therapeutic agent, and particularly without requiring a pre-existing ligand with high affinity and specificity to the target, would be desirable. This need and other needs are satisfied by the present invention.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

The present invention, in its various aspects, overcomes the drawbacks of the current state of the art described above. It can do so by providing for the development of small molecule therapeutic agents that allow the disruption of protein-protein interactions. This can be accomplished without requiring a pre-existing ligand with high affinity and specificity to the target.

In accordance with the purpose(s) of the invention, as embodied and broadly described herein, the invention, in one aspect, relates to inhibitors of protein-protein interactions, and more specifically to methods of creating protein-small molecule composite surfaces as inhibitors of protein-protein interactions.

Disclosed are methods of inhibiting a binding event between a target protein and a binding protein, comprising: administering to a cell in vitro an effective amount of a non-naturally occurring bifunctional inhibitor molecule including (a) protein binding moiety, and (b) an effector region; wherein said protein binding moiety binds to a blocking protein; and wherein said effector region binds to said target protein; in order to bind the target protein and the blocking protein and prevent access of the binding protein to the target protein.

Also disclosed are compounds comprising (a) protein binding moiety and (b) an effector region, wherein said protein binding moiety binds to a blocking protein, and wherein said effector region binds to a target protein.

Also disclosed are libraries comprising a multiplicity of bifunctional inhibitor molecules, each of said molecules comprising (a) protein binding moiety and (b) an effector region, wherein said protein binding moiety binds to a blocking protein, and wherein said effector region binds to a target protein.

Also disclosed are methods of preparing a non-naturally occurring bifunctional inhibitor molecule, the method comprising the step of covalently bonding a protein binding moiety to an effector region.

Also disclosed are methods of treating a patient having a disorder comprising the step of administering a non-naturally occurring bifunctional inhibitor molecule in an amount effective to treat the disorder in the patient.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Incubation of Protein G-beads with anti-Myc antibodies (1 μg), RalGDS-Myc tag (~100 nM), Texas Red-GST-KRas G12V (~100 nM) plus C12 (10 μM) or D38 (10 μM)

Figure 14:
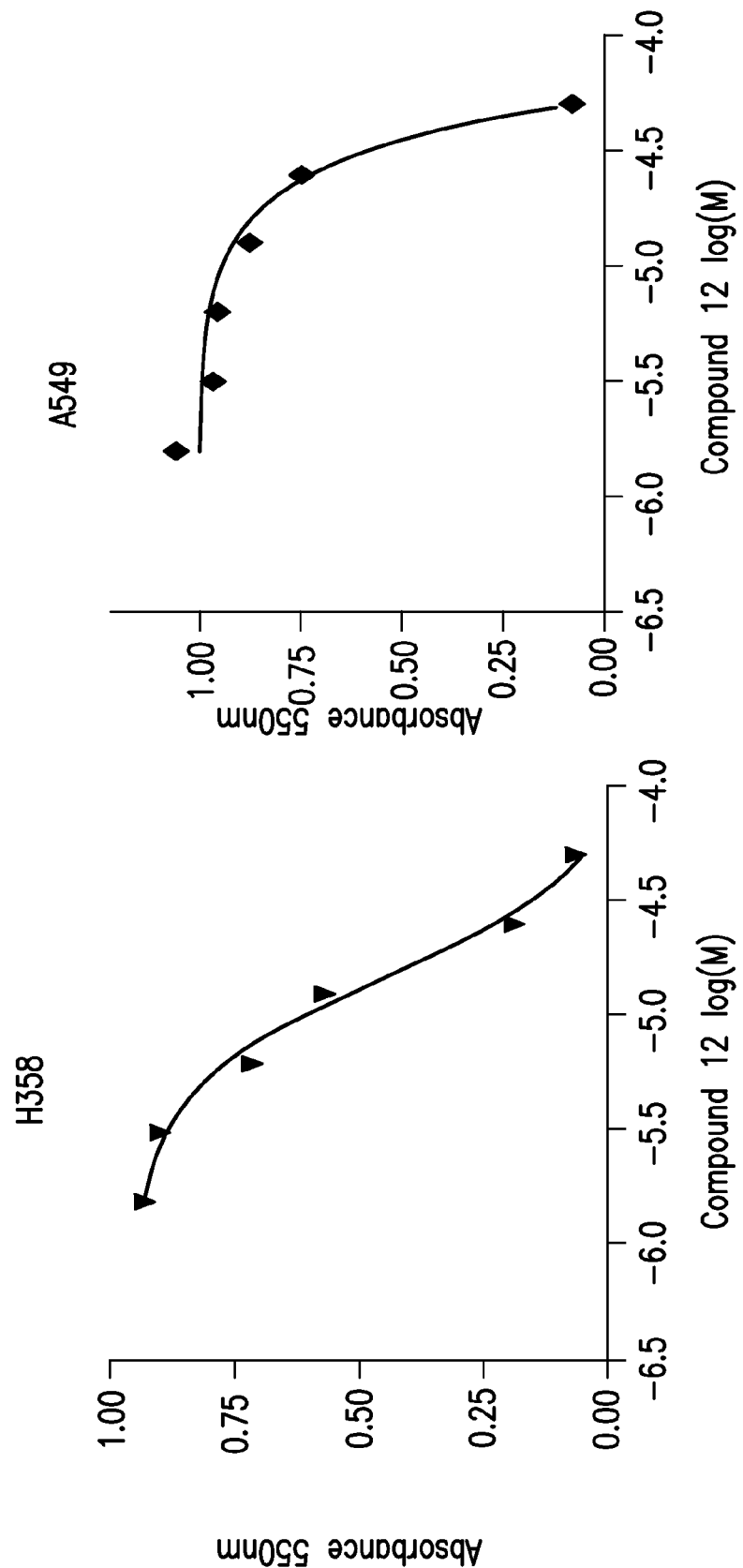

FIG. 14. MTT viability assay with H358 and A549 lung cancer cell lines (both have mutant K-Ras). The assay was performed to assess the effect of compound B12 on proliferation and survival of these cell lines. H358 cells were found to be sensitive to compound B12 whereas A549 cells are significantly less sensitive.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound 1f given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "ligand" refers to a a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the terms "effective amount" and "amount effective" refer to an amount that is sufficient to achieve the desired result or to have an effect on an undesired condition.

As used herein, "$EC_{50}$," is intended to refer to the concentration of a substance (e.g., a compound or a drug) that is required for 50% activation or enhancement of a biological process, or component of a process. For example, $EC_{50}$ can refer to the concentration of agonist that provokes a response halfway between the baseline and maximum response in an appropriate assay of the target activity.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay.

In the context of chemical formulas, the symbol "—" means a single bond, "=" means a double bond, and "≡" means triple bond. The symbol "----" represents an optional bond, which if present is either single or double. The symbol ⇌ represents a single bond or a double bond. Thus, for example, the structure

includes the structures

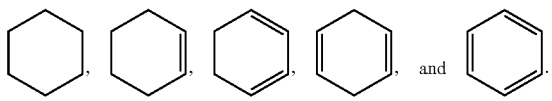

As will be understood by a person of skill in the art, no one such ring atom forms part of more than one double bond. The symbol "〰", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂▬" means a single bond where the group attached to the thick end of the wedge is "out of the page." The symbol "⫽⫽⫽" means a single bond where the group attached to the thick end of the wedge is "into the page". The symbol "〰" means a single bond where the conformation (e.g., either R or S) or the geometry is undefined (e.g., either E or Z).

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10), or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

When used in the context of a chemical group, "hydrogen" means —H; "hydroxy" and "hydroxyl" can be used interchangeably and mean —OH; "oxo" means =O; "halo," "halogen" and "halide", as used herein can be used interchangeably, mean independently —F, —Cl, —Br or —I; "amino" means —NH$_2$; "hydroxyamino" means —NHOH; "nitro" means —NO$_2$; imino means =NH; "cyano" and "nitrile" can be used interchangeably and mean —CN; "isocyanate" means —N=C=O; "azido" means —N$_3$; in a monovalent context "phosphate" means —OP(O)(OH), or a deprotonated form thereof; in a divalent context "phosphate" means —OP(O)(OH)O— or a deprotonated form thereof; "mercapto" and "thiol" can be used interchangeably and mean —SH; and "thio" means =S; "sulfonyl" means —S(O)$_2$—; and "sulfinyl" means —S(O)—.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$—CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atoms has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH₃ (Me), —CH₂CH₃ (Et), —CH₂CH₂CH₃ (n-Pr), —CH(CH₃)₂ (iso-Pr), —CH(CH₂)₂ (cyclopropyl), —CH₂CH₂CH₂CH₃ (n-Bu), —CH(CH₃) CH₂CH₃ (sec-butyl), —CH₂CH(CH₃)₂ (iso-butyl), —C(CH₃)₃ (tert-butyl), —CH₂C(CH₃)₃ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH₂— (methylene), —CH₂CH₂—, —CH₂C(CH₃)₂CH₂—, —CH₂CH₂CH₂—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH₂, =CH(CH₂CH₃), and =C(CH₃)₂. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. An "alkane" refers to the compound H—R, wherein R is alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. The term "halogenated alkyl" or "haloalkyl" is a subset of substituted alkyl, in which one or more hydrogens has been substituted with a halo group (i.e., fluorine, chlorine, bromine, or iodine) and no other atoms aside from carbon, hydrogen and halogen are present. The group, —CH₂Cl is a non-limiting example of a haloalkyl. The term "fluoroalkyl" is a subset of substituted alkyl, in which one or more hydrogens has been substituted with a fluoro group and no other atoms aside from carbon, hydrogen and fluorine are present. The groups, —CH₂F, —CF₃, and —CH₂CF₃ are non-limiting examples of fluoroalkyl groups. An "alkane" refers to the compound H—R, wherein R is alkyl. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "alkoxy" when used without the "substituted" modifier refers to the group —OR, in which R is an alkyl, as that term is defined above. Non-limiting examples of alkoxy groups include: —OCH₃, —OCH₂CH₃, —OCH₂CH₂CH₃, —OCH(CH₃)₂, —OCH(CH₂)₂, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The term "alcohol" corresponds to an alkane, as defined above, wherein at least one of the hydrogen atoms has been replaced with a hydroxy group.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "cycloalkenyl" as used herein is a non-aromatic carbon-based ring composed of at least three carbon atoms and containing at least one carbon-carbon double bound, i.e., C=C. Cycloalkenyl is a subset of alkenyl. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "alkynyl" when used without the "substituted" modifier refers to a monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C=CH, —OCCH$_3$, and —CH$_2$C=CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "cycloalkynyl" as used herein is a non-aromatic carbon-based ring composed of at least seven carbon atoms and containing at least one carbon-carbon triple bound, and is a subset of those groups specified by the term "alkynyl." Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

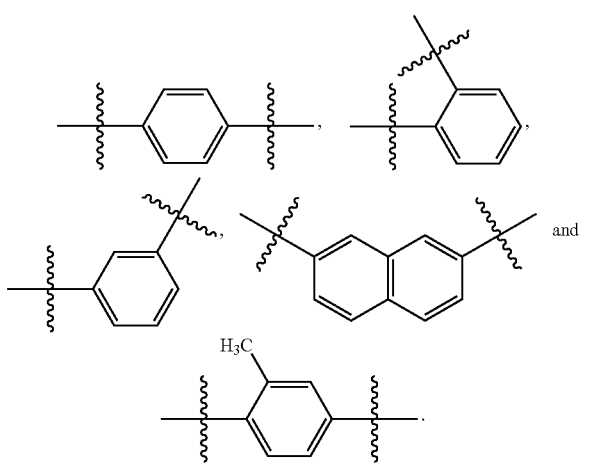

When the term "aryl" is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aldehyde" as used herein is represented by the formula —C(O)H. Throughout this specification "C(O)" is a short hand notation for a carbonyl group, i.e., C═O.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group ═NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "carboxylic acid" as used herein is represented by the formula —C(O)OH.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

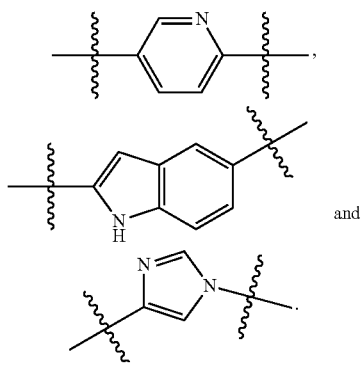

When the term "heteroaryl" is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The terms "heterocycle" or "heterocyclyl," as used herein can be used interchangeably and refer to single and multicyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazepinyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfone"

as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Suitable monovalent substituents on a substitutable carbon atom of an "optionally substituted" group are independently halogen; $-(CH_2)_{0-4}R^\circ$; $-(CH_2)_{0-4}R^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}-O-(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_1-$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "stable," as used herein, refers to compounds that are not substantially altered when subjected to conditions to allow for their production, detection, and, in certain aspects, their recovery, purification, and use for one or more of the purposes disclosed herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

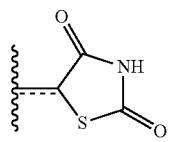

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^8F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

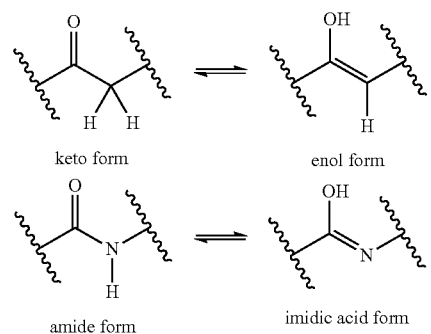

keto form   enol form amide form   imidic acid form

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Any undefined valency on an atom of a structure shown in this application implicitly represents a hydrogen atom bonded to the atom. When a group "R" is depicted as a "floating group" on a ring system, for example, in the formula:

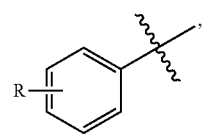

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

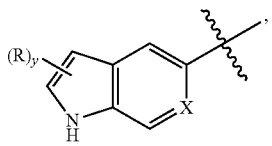

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

The above definitions supersede any conflicting definition in any of the references that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

A. INHIBITORS OF PROTEIN-PROTEIN INTERACTIONS

Figure 1A:
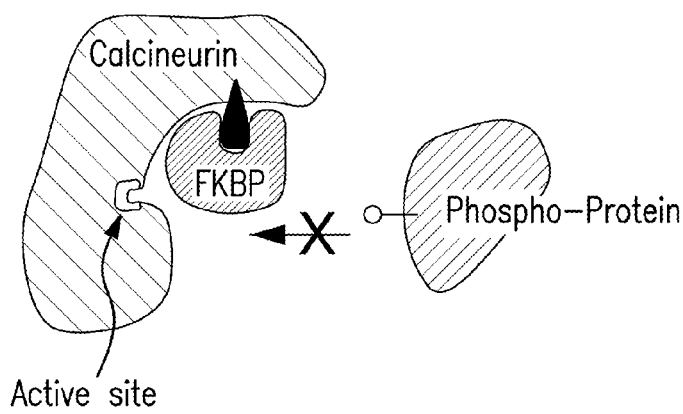
FIG. 1 shows the mechanism by which FK506-FKBP inhibits calcineurin.
Figure 1B:
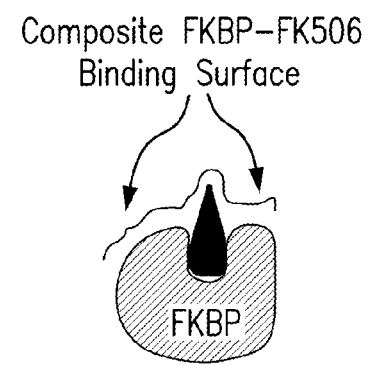

The inhibition of PPIs with small molecules does occur in nature, as exemplified by the mode of action of the immunosuppressant FK506. FK506 binds to the cytosolic FK506-binding-protein 12 (FKBP) to form a binary complex. Part of the FK506 molecule (the FKBP-binding moiety) is deeply buried in FKBP, while the other part (the so-called effector domain) sticks out of the FKBP surface (see FIG. 1). The FK506-FKBP complex then binds to and inhibits phosphatase calcineurin, resulting in immunosuppression. Unlike conventional enzyme inhibitors, FK506-FKBP does not bind to the active site of calcineurin. Rather, it binds at a site distant from the active site but sterically blocks the entry of protein substrates into the phosphatase active site (FIG. 1).[1] FK506 by itself binds only very weakly to calcineurin. The high binding affinity between the FK506-FKBP complex and calcineurin (Ki=6 nM)[3] is achieved by both FK506 and FKBP making favorable interactions with calcineurin[4]. Mutation of FKBP residues (e.g., Arg421) was shown to greatly reduce the FK506-FKBP affinity for calcineurin.[3]

In addition to FK506, several other natural products including rapamycin, meridamycin, and antascomicins A-E also bind to FKBP with high affinity and their binary complexes act as inhibitors of important proteins. For example, the target of the FKBP-rapamycin complex is the signaling protein mTOR[5,6] (the molecular targets of the other two complexes are currently unknown).

More specifically, FK506 and rapamycin are natural products that are produced by soil microorganisms. Both molecules are effective immunosuppressive drugs that are used for organ transplantation[26,27]. In addition, rapamycin has shown activity as an anti-cancer agent[28]. As described above, the molecular target of FK506 is the protein phosphatase calcineurin. The molecular target of rapamycin is a protein kinase, mammalian target of rapamycin (mTOR). Unlike most small-molecules drugs, FK506 and rapamycin by themselves show only very modest affinity for their respective targets. To be efficacious, FK506 and rapamycin must first form a binary complex with the endogenous FKBP, a peptidyl-prolyl isomerase that is widely expressed in human cells. The resulting FK506-FKBP and rapamycin-FKBP complexes bind with high affinity and specificity and inhibit the enzymatic activities of calcineurin and mTOR, respectively[29-32]. Compared to the drugs alone, the drug-FKBP binary complexes show increased binding affinities because the FKBP protein surface also makes favorable molecular interactions with the target protein surface[33]. Thus, by binding to FKBP, FK506 and rapamycin create composite binding surfaces that allow both drug-target and FKBP-target interactions.

Figure 2:
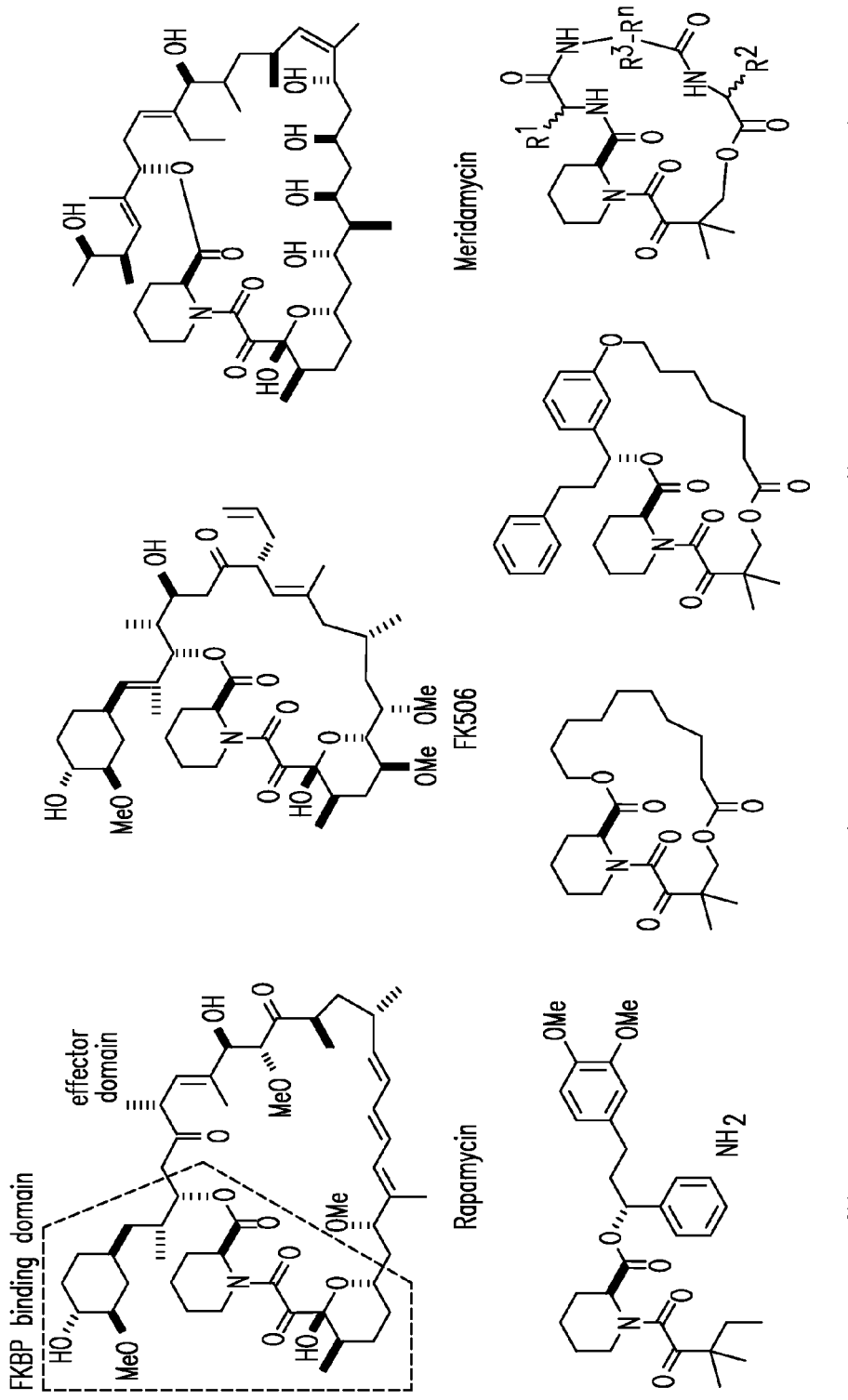
FIG. 2 shows structures of FK506, rapamycin, meridamycin, and rapalogs SLF, 1 and 2.

FK506 and rapamycin are bifunctional molecules (FIG. 2). One part of the molecules binds to FKBP, while the second part (the effector domain) interacts with the target protein and provides target specificity. The co-crystal structures of FK506-FKBP-calcineurin and rapamycin-FKBP-mTOR reveal that the composite FKBP-drug binding surfaces are large and bind to relatively flat surfaces on their target proteins[34-36]. The two-dimensional binding character of the composite FKBP-drug binding surface is in stark contrast to that of most small-molecule drugs, which typically bind in deep binding pockets that provide three-dimensional binding spaces. A deep binding pocket in a target protein allows for the establishment of many molecular interactions between a small molecule and the protein so that high affinity binding can occur. Proteins with distinct binding pockets are usually enzymes, ion channels and receptors. These classes of proteins make up the majority of all drug targets that have already been exploited[37]. On the other hand, many potential drug targets exert their biological activities through protein-protein interactions. Protein-protein interactions often take place via large and flat surfaces that are considered "undruggable" because small molecules cannot establish sufficient molecular interactions with these flat target surfaces in order to bind with high affinity and selectivity.

Through the formation of composite drug-FKBP binding surfaces, a solution to successfully target flat protein surfaces with small molecules has been provided in nature. In addition to FK506 and rapamycin, meridamycin, a macrolide produced by the soil bacterium *Streptomyces hygroscopicus*, is also a high-affinity FKBP ligand that antagonizes the immunosuppressive activity of FK506[38]. The molecular target of the meridamycin-FKBP complex is currently unknown. Likewise, antascomicins A-E bind to FKBP with about the same nanomolar affinity as FK506 and rapamycin and the antascomycin-FKBP complexes inhibits the function of a yet unknown cellular target(s)[39].

Aside from FKBP, other proteins in nature form composite binding surfaces. One such example is the peptidyl-prolyl isomerase cyclophilin A (CypA). The natural products that bind to cyclophilin to form drug-protein complexes include cyclosporin A (CsA) and sanglifehrin A. CsA is a cyclic undecapeptide and the CsA-CypA complex creates a composite surface that also binds and inhibits calcineurin[7]. Again, both CsA and CypA make molecular contacts with calcineurin and contribute to the overall affinity and specificity[8]. Sanglifehrin A has shown exceptionally high affinity for CypA in a cell free assay (IC50=~7 nM)[9]. The Sanglifehrin-CypA complex has immunosuppressive activity, although the target of the complex remains to be identified.

Although FKBP and cyclophilin share little structural similarity, they are both peptidyl-prolyl isomerases, which catalyze the isomerization of peptidyl-prolyl bonds (cis↔trans) in proteins. FKBP and cyclophilin are ubiquitously expressed at high concentrations ($\mu$M) in all human cells. They are in fact among the most abundant proteins found in human cells. As chaperones, FKBP and cyclophilin have evolved to interact with a large number of protein surfaces. Thus, the FK506-, rapamycin-, meridamycin-, antascomycin-, cyclosporine- and sanghliferin-chaperone complexes are enabled by the chaperone characteristics of FKBP and cyclophilin to bind to relatively flat target surfaces with high affinity and to disrupt PPIs due to their steric bulk.

The mode-of-action of the FK506-FKBP complex can be compared to an antibody therapeutic. First, like an inhibitory antibody, the FK506-FKBP complex binds to a relatively flat target surface by establishing many molecular interactions that cover a large area. Second, the FK506-FKBP complex exerts its activity based on steric hindrance. Because of the analogies to an inhibitory antibody, herein the term "chemobody" is used to describe a complex like FK506-FKBP. The defining characteristic of FK506 as a small molecule is its bifunctionality. One part of FK506 constitutes a binding moiety for FKBP, while the other part serves as the effector domain that defines the target specificity of the resulting chemobody.

Despite the different effector domains of FK506, rapamycin, meridamycin and antascomycins, which allow them to bind to different target proteins, the four compounds possess a common FKBP-binding moiety, which consists of a triketo pipecolyl core (FIG. 2). One aspect of the present invention involves the generalization of the mechanism-of-action of FK506 and rapamycin to target otherwise intractable protein sites. More specifically, this aspect generalizes the mode-of-action of FK506-FKBP to inhibit PPIs of interest by synthesizing bifunctional molecules that can form artificial chemobodies with FKBP. These molecules would each contain a common FKBP binding moiety and a unique effector domain. When such a molecule enters the cell, it would bind to the endogenous FKBP to form a chemobody, which in turn binds and inhibits the function of a target protein. By this process is provided a general approach to designing drugs against PPI targets, which have generally been considered intractable to date.

Such an aspect of the present invention thus may provide a method of inhibiting a binding event between a target protein and a binding protein, comprising administering to a cell in vitro an effective amount of a non-naturally occurring bifunctional inhibitor molecule including (a) protein binding moiety, and (b) an effector region, wherein the protein binding moiety binds to a blocking protein, and wherein the effector region binds to the target protein, in order to bind the target protein and the blocking protein and prevent access of the binding protein to the target protein. This aspect of the present invention also then provides the bifunctional inhibitor molecule to interrupt the protein-protein interaction.

Another aspect of the present invention provides a synthetic route that allows the rapid synthesis of large libraries of cyclic bifunctional molecules. These synthetic molecules (or "rapalogs," as they may be referred to herein) include a common FKBP-binding moiety but different effector domains which replace the calcineurin/mTOR-binding motifs of FK506/rapamycin (compound 2, FIG. 2). When bound to FKBP, these rapalogs should create diverse composite binding surfaces on FKBP, which may be screened for binding to otherwise intractable protein targets.

A third aspect of the present invention provides a screening method for identifying the active rapalog(s) from large libraries of cyclic bifunctional molecules. The screening method involves incubating one-bead-one-compound libraries with FKBP and the target protein labeled with different fluorescent dyes (e.g., green for FKBP and red for target protein). A positive bead containing a bifunctional molecule recruits both proteins to its surface and is fluorescent in both green and red colors.

Thus, one aspect of the present invention provides for the generalization of a large library of rapalogs that retain the ability to bind to FKBP but each have a different effector domain in order to provide a diverse array of composite surfaces for screening against proteins that exert their activity through protein-protein interactions. To achieve this goal, a minimal structural unit that is sufficient for binding to FKBP with high affinity and specificity was first derived. Next, the effector domain of rapamycin was replaced with structurally diverse moieties. Short peptides were initially chosen as the effector domains, because a large number of different peptides can be generated from a small set of amino acid building blocks and peptides are synthetically accessible. However, the present invention is not limited to short peptides as the effector domains, as other types of structures may also be used (as will be recognized by those of ordinary skill in the art).

Figure 3:
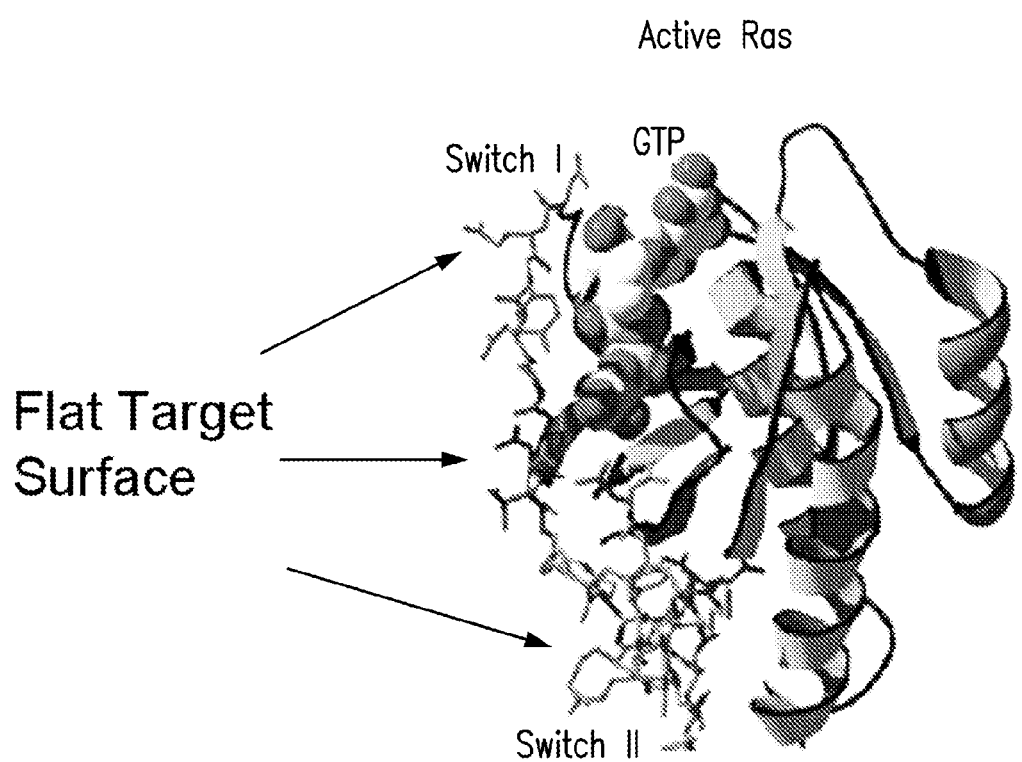
FIG. 3 shows Ras-GTP co-crystal structure.

Another aspect of the present invention provides a K-Ras inhibitor. Ideally, a K-Ras inhibitor should disrupt the interactions between Switch I/II and the effector proteins that bind at these sites. The Switch I/II regions constitute flat surfaces which are notoriously difficult to target with conventional small molecules (FIG. 3). It is believed that K-Ras is a suitable target for chemobody inhibitors. The Switch I/II regions interact with more than 10 different K-Ras effector proteins. There is no homology among these proteins that would suggest the existence of a canonical "K-Ras binding domain". Hence, the Switch I/II peptides appear to generate "sticky surfaces[17]" that are able to accommodate many different protein surfaces. Thus, it should be possible to generate a composite rapalog-FKBP surface that can interact with the K-Ras surface with high affinity. Moreover, when a chemobody is bound to the Switch I/II region, it should create a steric block that prevents the binding of K-Ras effector proteins at the Switch I/II site and possibly neighboring surfaces.

Herein, the following abbreviations may be used: CypA, peptidyl-prolyl isomerase cyclophilin A; CsA, cyclosporin A; SAR, structure-activity relationship; D-Abu, (S)-2-aminobutyric acid; D-β-homoPhe, (R)-3-amino-5-phenylpentanoic acid; L-β-homoPhe, (S)-3-amino-5-phenylpentanoic acid; D-homoPhe, D-homophenylalanine; L-β-Ile, L-β-isoleucine; HBTU, O-benzotriazole-N,N,N,N-tetramethyluronium hexafluorophosphate; NMM, N-methylmorpholine; PyBop, benzotriazole-1-yl-oxytripyrrolidinophosphonium hexafluorophosphate; DMAP, 4-(dimethylamino) pyridine; FA, fluorescence anisotropy; OBOC, one-bead-one-compound; HOBt, 1-hydroxybenzotriazole hydrate.

B. COMPOSITIONS

In one aspect, the invention relates to compounds comprising (a) protein binding moiety and (b) an effector region, wherein said protein binding moiety binds to a blocking protein, and wherein said effector region binds to a target protein.

In a further aspect, a compound can have a structure represented by a formula:

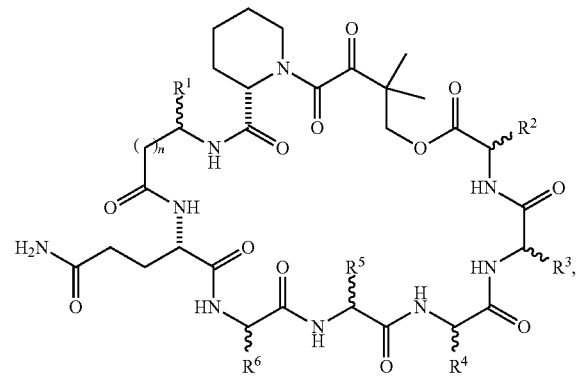

wherein n is 0 or 1; wherein each of $R^1$-$R^6$ is selected to comprise, together with the attached amino acid, a residue selected from Ala, Gly, Ser, Pro, Ile, Gln, Glu, His, Arg, Tyr, Trp, Orn, Phg, L-Phe(Fpa), nal, nle, D-Ala, D-Val, D-Pro, D-Thr, D-Leu, D-Asn, D-Lys, D-Phe, and D-Asp.

In a further aspect, $R^1$ is selected from hydrogen, methyl, ethyl, propyl, phenyl, butyl, benzyl, and 2-ethylphenyl, or $R^1$ and its attached amino acid comprise a residue of L-Ala, D-Abu, D-β-Glu, D-homoPhe, L-β-Ile, L-Ile, D-Ile, L-β-homoPhe, or D-β-homoPhe; $R^2$ is selected from hydrogen, methyl, and ethyl, or $R^2$ and its attached amino acid comprise a residue of D-Ala, L-Phe, or L-Thr; $R^3$ is selected from hydrogen, methyl, and ethyl, or $R^3$ and its attached amino acid comprise a residue of L-Ala or D-Ala; $R^4$ is selected from hydrogen, methyl, and ethyl, or $R^4$ and its attached amino acid comprise a residue of L-Ala or D-Ala; $R^5$ is selected from hydrogen, methyl, and ethyl, or $R^5$ and its attached amino acid comprise a residue of L-Ala or D-Ala; and $R^6$ is selected hydrogen, methyl, and ethyl, or $R^6$ and its attached amino acid comprise a residue of L-Ala or D-Ala.

In a further aspect, $R^1$ is 2-ethylphenyl. In a further aspect, $R^2$ and its attached amino acid comprise a residue of D-Ala, L-Phe, or L-Thr. In a further aspect, $R^3$ and its attached amino acid comprise a residue of L-Ala or D-Ala. In a further aspect, $R^4$ and its attached amino acid comprise a residue of L-Ala or D-Ala. In a further aspect, $R^5$ and its attached amino acid comprise a residue of L-Ala or D-Ala. In a further aspect, $R^6$ and its attached amino acid comprise a residue of L-Ala or D-Ala.

In a further aspect, a compound has a structure represented by a formula:

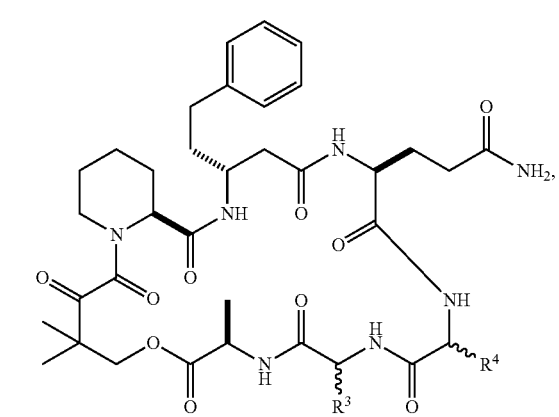

wherein R³ is selected from hydrogen, methyl, and ethyl, or wherein R³ and its attached amino acid comprise a residue of L-Ala or D-Ala; and wherein R⁴ is selected from hydrogen, methyl, and ethyl, or wherein R⁴ and its attached amino acid comprise a residue of L-Ala or D-Ala.

In a further aspect, a compound has a structure represented by a formula:

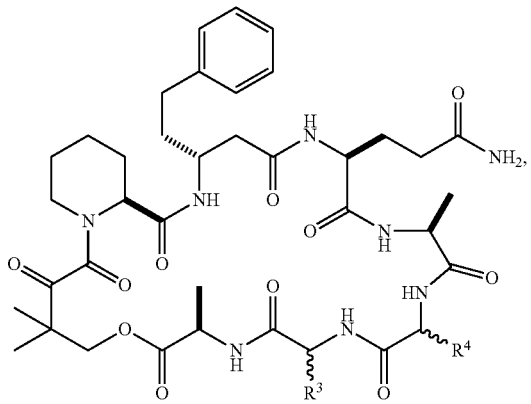

wherein R³ is selected from hydrogen, methyl, and ethyl, or wherein R³ and its attached amino acid comprise a residue of L-Ala or D-Ala; and wherein R⁴ is selected from hydrogen, methyl, and ethyl, or wherein R⁴ and its attached amino acid comprise a residue of L-Ala or D-Ala.

Figure 4:
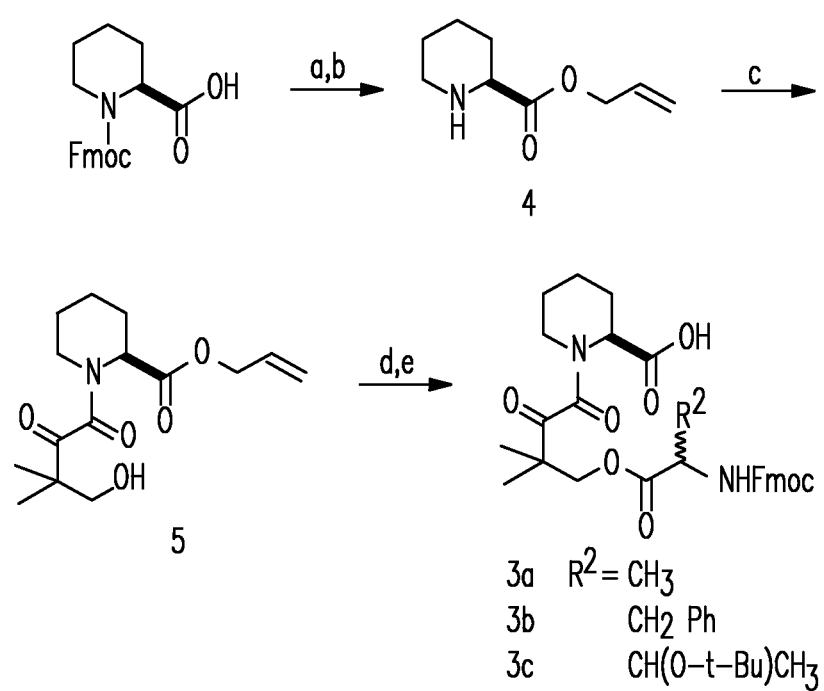
FIG. 4 shows the synthetic route for key building blocks of rapalog libraries where the reagents and conditions are as follows: a) 5 equiv allyl bromide, 2 equiv $Cs_2CO_3$, acetone, 2 h; b) 20% piperidine in DCM, 20 min; c) 1.5 equiv dihydro-4,4-dimethyl-2,3-furandione, 10% DMAP, Ar gas, toluene, reflux, overnight; d) DIC, Fmoc-amino acids ($R_2$), 5% DMAP, 1 h; e) 5% $Pd(Ph_3P)_4$, 3 equiv N-methylaniline, THF.
Figure 5:
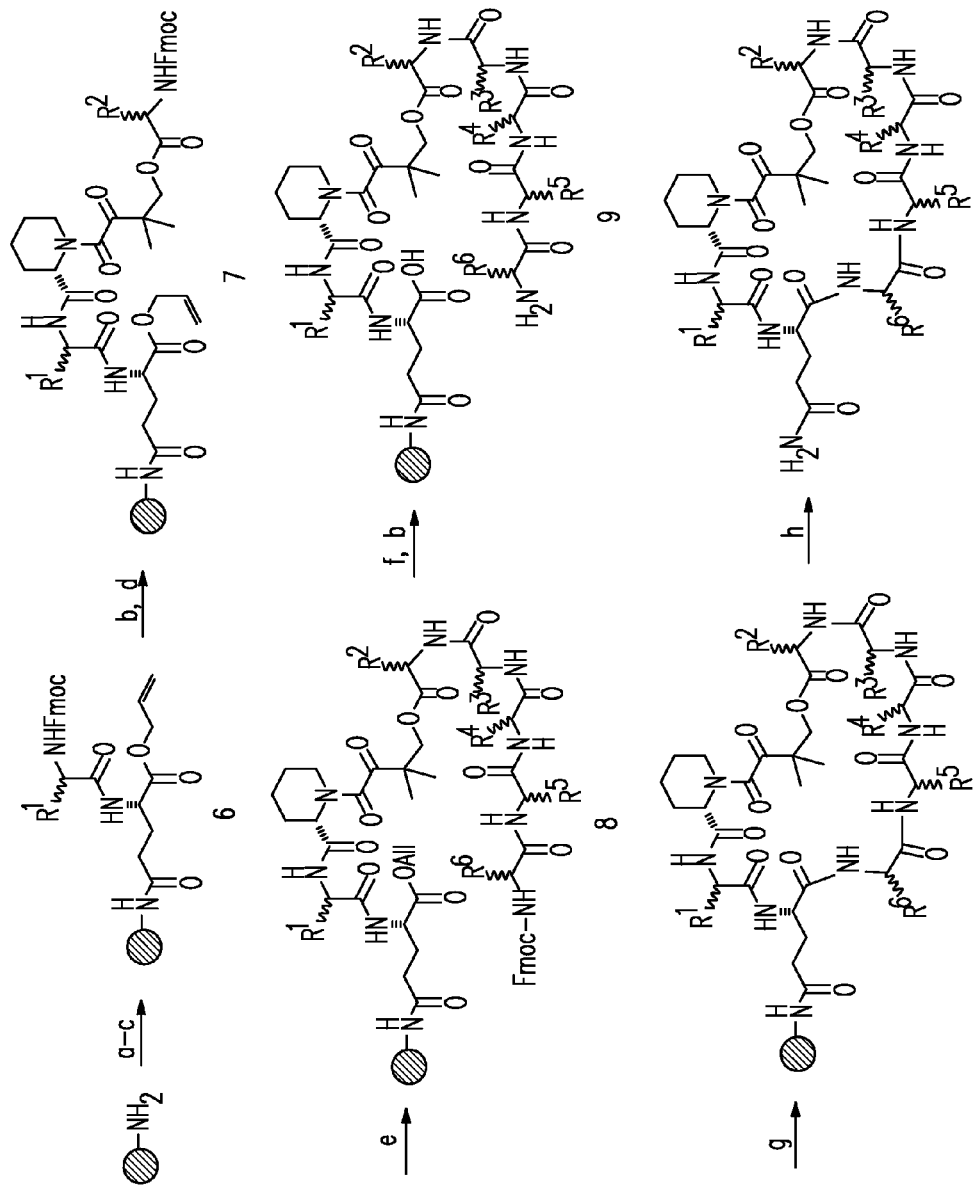
FIG. 5 shows the synthesis of a rapalog library where the reagents and conditions are as follows: (a) soak in water; 0.5 equiv Fmoc-Glu(NHS)—O-allyl; then excess Fmoc-Glu(tBu)-OH/HBTU; (b) piperidine; (c) Fmoc-β-HomoPhe/HBTU; (d) building block 4, HBTU; (e) split-and-pool synthesis with Fmoc peptide chemistry; (f) $Pd(PPh_3)_4$; (g) PyBOP; and (h) TFA, TIPS.
Figure 8:
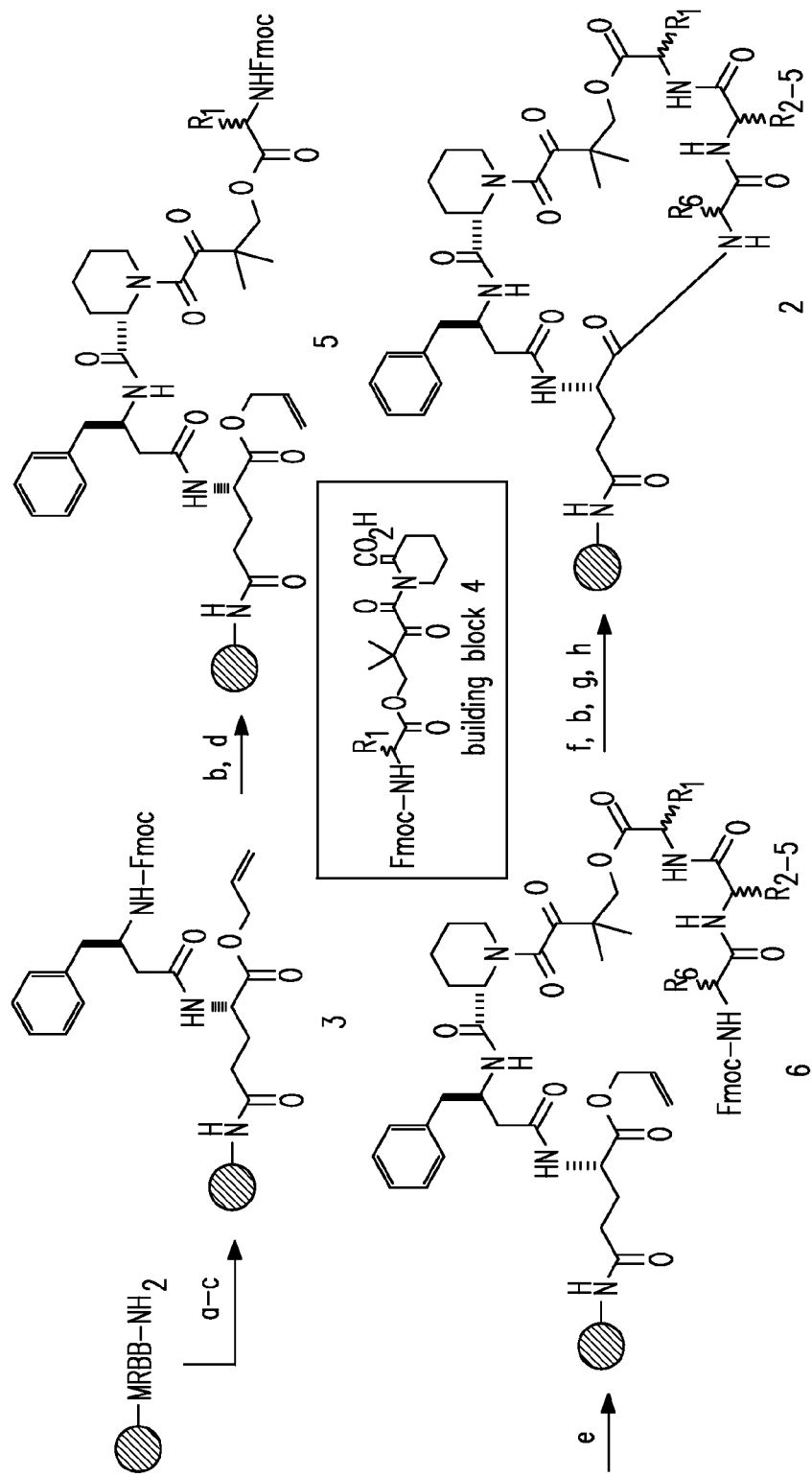
FIG. 8 Synthesis of the rapalog library (C series). Reagents and conditions: (a) soak in water; 0.5 equiv Fmoc-Glu (NHS)—O-allyl; then excess Fmoc-Glu(tBu)-OH/HBTU; (b) piperidine; (c) Fmoc-b-HomoPhe/HBTU; (d) building block 4, HBTU; (e) split-and-pool synthesis with Fmoc peptide chemistry; (f) $Pd(PPh_3)_4$; (g) PyBOP; and (h) TFA, TIPS.

The disclosed compounds can be prepared, for example, according to the synthetic procedures outlines in FIGS. 4, 5, and 8.

In one aspect, the invention relates to libraries comprising a multiplicity of bifunctional inhibitor molecules, each of said molecules comprising (a) protein binding moiety and (b) an effector region, wherein said protein binding moiety binds to a blocking protein, and wherein said effector region binds to a target protein. For example, the libraries can include one or more compounds disclosed herein.

C. METHODS

In one aspect, the invention relates to methods of inhibiting a binding event between a target protein and a binding protein, comprising: administering to a cell in vitro an effective amount of a non-naturally occurring bifunctional inhibitor molecule including (a) protein binding moiety, and (b) an effector region; wherein said protein binding moiety binds to a blocking protein; and wherein said effector region binds to said target protein; in order to bind the target protein and the blocking protein and prevent access of the binding protein to the target protein. In a further aspect, said blocking protein is FKBP. In a further aspect, the molecule is a cyclic molecule. In a further aspect, the target protein is K-Ras.

In one aspect, the invention relates to methods of preparing a non-naturally occurring bifunctional inhibitor molecule, the method comprising the step of covalently bonding a protein binding moiety to an effector region. In a further aspect, the effector region is generated randomly prior to the bonding step.

In one aspect, the invention relates to methods of treating a patient having a disorder comprising the step of administering a non-naturally occurring bifunctional inhibitor molecule in an amount effective to treat the disorder in the patient. In a further aspect, the bifunctional inhibitor molecule comprises a compound having (a) a protein binding moiety and (b) an effector region. In a further aspect, the compound exhibits immunosuppressive effect. In a further aspect, the compound exhibits antiproliferative effect.

D. FURTHER ASPECTS OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described above, the present invention, in its various aspects, overcomes the drawbacks of the current state of the art described above. It does so by providing for the development of small molecule therapeutic agents that allow the disruption of protein-protein interactions. This may be accomplished without requiring a pre-existing ligand with high affinity and specificity to the target.

Further, as described above, despite the different effector domains of FK506, rapamycin, meridamycin and antascomycins, which allow them to bind to different target proteins, the four compounds possess a common FKBP-binding moiety, which consists of a triketo pipecolyl core (FIG. 2). One aspect of the present invention involves the generalization of the mechanism-of-action of FK506 and rapamycin to target otherwise intractable protein sites. More specifically, this aspect generalizes the mode-of-action of FK506-FKBP to inhibit PPIs of interest by synthesizing bifunctional molecules that can form artificial chemobodies with FKBP. These molecules would each contain a common FKBP binding moiety and a unique effector domain. When such a molecule enters the cell, it would bind to the endogenous FKBP to form a chemobody, which in turn binds and inhibits the function of a target protein. By this process is provided a general approach to designing drugs against PPI targets, which have generally been considered intractable to date.

Such an aspect of the present invention thus may provide a method of inhibiting a binding event between a target protein and a binding protein, comprising administering to a cell in vitro an effective amount of a non-naturally occurring bifunctional inhibitor molecule including (a) protein binding moiety, and (b) an effector region, wherein the protein binding moiety binds to a blocking protein, and wherein the effector region binds to the target protein, in order to bind the target protein and the blocking protein and prevent access of the binding protein to the target protein. This aspect of the present invention also then provides the bifunctional inhibitor molecule to interrupt the protein-protein interaction.

Another aspect of the present invention provides a synthetic route that allows the rapid synthesis of large libraries of cyclic bifunctional molecules. These synthetic molecules (or "rapalogs," as they may be referred to herein) include a common FKBP-binding moiety but different effector domains which replace the calcineurin/mTOR-binding motifs of FK506/rapamycin (compound 2, FIG. 2). When bound to FKBP, these rapalogs should create diverse composite binding surfaces on FKBP, which may be screened for binding to otherwise intractable protein targets.

Thus, one aspect of the present invention provides for the generalization of a large library of rapalogs that retain the ability to bind to FKBP but each have a different effector domain in order to provide a diverse array of composite surfaces for screening against proteins that exert their activity through protein-protein interactions. To achieve this goal, a minimal structural unit that is sufficient for binding to FKBP with high affinity and specificity was first derived. Next, the effector domain of rapamycin was replaced with structurally diverse moieties. Short peptides were initially chosen as the effector domains, because a large number of different peptides can be generated from a small set of amino acid building blocks and peptides are synthetically accessible. However, the present invention is not limited to short peptides as the effector domains, as other types of structures may also be used (as will be recognized by those of ordinary skill in the art).

Another aspect of the present invention provides a K-Ras inhibitor. Ideally, a K-Ras inhibitor should disrupt the interactions between Switch I/II and the effector proteins that bind at these sites. The Switch I/II regions constitute flat surfaces which are notoriously difficult to target with conventional small molecules (FIG. 3). It is believed that K-Ras is a suitable target for chemobody inhibitors. The Switch I/II regions interact with more than 10 different K-Ras effector proteins. There is no homology among these proteins that would suggest the existence of a canonical "K-Ras binding domain". Hence, the Switch I/II peptides appear to generate "sticky surfaces 17" that are able to accommodate many different protein surfaces. Thus, it should be possible to generate a composite rapalog-FKBP surface that can interact with the K-Ras surface with high affinity. Moreover, when a chemobody is bound to the Switch I/II region, it should create a steric block that prevents the binding of K-Ras effector proteins at the Switch I/II site and possibly neighboring surfaces.

As described above, one aspect of the present invention is the synthesis of a large library of rapalogs that retain the ability to bind to FKBP but that each also has a different effector domain in order to create a diverse array of composite surfaces for screening against a target protein. To achieve this aspect of the present invention requires (1) devising a minimal structural unit that is capable of binding to FKBP with high affinity and specificity (i.e., identifying a minimal FKBP-binding motif), and (2) replacing the effector domain of rapamycin with structurally diverse moieties. In the work described below and as described above, peptides are described as the effector domains, because peptides of diverse structures can be generated from a small set of amino acid building blocks and are synthetically accessible. However, those of ordinary skill in the art will recognize that other structures may be used as the effector domains, and the present invention is not limited to peptides as the effector domains.

1. Identification of a Minimal FKBP-Binding Motif.

As described above, a first step is devising a minimal structural unit that is capable of binding to FKBP with high affinity and specificity (i.e., identifying a minimal FKBP-binding motif). Previous work of Holt et al. has established that a macrocycle containing a 3,3-dimethyl-2-ketobutyryl-L-pipecolinate (Dkb-Pip) core (1a, FIG. 2) is sufficient to retain much of the FKBP-binding activity of rapamycin (apparent KI of 30 nM)$_{2-0}$. Addition of an (R)-1-(phenylethyl) benzyl group to the core increased the binding affinity by 30-fold. To facilitate later library synthesis, the (R)-1-(phenylethyl)benzyl moiety was replaced with a simpler building block such as an amino acid (R1 in 2, FIG. 2). In addition, it was believed that the residue immediately N-terminal to the Dkb-Pip core (R2 in 2, FIG. 2) might also affect FKBP binding.

To identify a competent, minimal FKBP-binding motif, 15 cyclic peptides (Table 1, compounds 2a-n) were designed that featured 10 different R1 residues including L-alanine, D-alanine, (S)-2-aminobutyric acid (D-Abu), (R)-3-aminoadipic acid (D-β-Glu), (R)-3-amino-5-phenylpentanoic acid (D-β-homoPhe), (S)-3-amino-5-phenylpentanoic acid (L-β-homoPhe), D-homophenylalanine (D-homoPhe), L-β-isoleucine (L-β-Ile), L-isoleucine, and D-isoleucine and three R2 residues (D-Ala, L-Thr, and L-Phe).

TABLE 1

SAR of Rapalogs 2a-y[a]

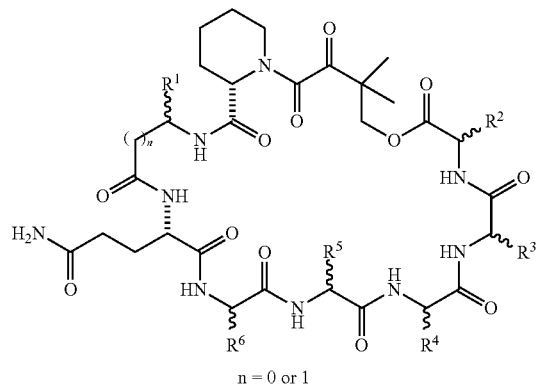

2 n = 0 or 1

| Compound | R$_1$ | R$_2$ | R$_3$ | R$_4$ | R$_5$ | R$_6$ | IC$_{50}$ (μM) |
|---|---|---|---|---|---|---|---|
| 2a | L-Ala | D-Ala | L-Ala | L-Ala | | | 240 ± 7 |
| 2b | D-Ala | D-Ala | L-Ala | L-Ala | | | 298 ± 80 |
| 2c | D-Abu | D-Ala | L-Ala | L-Ala | | | 303 ± 27 |
| 2d | D-β-Glu | D-Ala | L-Ala | L-Ala | | | 310 ± 2 |
| 2e | D-β-homoPhe | D-Ala | L-Ala | L-Ala | | | 13 ± 4 |
| 2f | D-homoPhe | D-Ala | L-Ala | L-Ala | | | 147 ± 23 |
| 2g | L-β-Ile | D-Ala | L-Ala | L-Ala | | | 165 ± 42 |
| 2h | L-Ile | D-Ala | L-Ala | L-Ala | | | 316 ± 46 |
| 2i | D-Ile | D-Ala | L-Ala | L-Ala | | | 266 ± 46 |
| 2j | L-β-homoPhe | L-Phe | L-Ala | L-Ala | | | 26 ± 3 |
| 2k | D-β-homoPhe | L-Phe | L-Ala | L-Ala | | | 18 ± 2 |
| 2l | L-β-Ile | L-Phe | L-Ala | L-Ala | | | 250 ± 57 |
| 2m | D-β-Glu | L-Phe | L-Ala | L-Ala | | | 386 ± 43 |
| 2n | D-β-homoPhe | L-Thr | L-Ala | L-Ala | | | 4 ± 1 |
| 2o | D-β-homoPhe | D-Ala | L-Ala | D-Ala | L-Ala | | 20 ± 6 |
| 2p | D-β-homoPhe | D-Ala | L-Ala | L-Ala | L-Ala | | 6 ± 2 |
| 2q | D-β-homoPhe | D-Ala | D-Ala | D-Ala | D-Ala | | 13 ± 2 |
| 2r | D-β-homoPhe | L-Thr | L-Ala | L-Ala | L-Ala | | 9 ± 3 |
| 2s | D-β-homoPhe | L-Phe | L-Ala | D-Ala | L-Ala | | 31 ± 6 |
| 2t | D-β-homoPhe | L-Phe | L-Ala | L-Ala | L-Ala | | 10 ± 1 |
| 2u | D-β-homoPhe | L-Thr | | | | | 37 ± 10 |
| 2v | D-βhomoPhe | D-Ala | | | | | 18 ± 6 |
| 2w | D-β-homoPhe | D-Ala | L-Ala | D-Ala | L-Ala | L-Ala | 13 ± 2 |
| 2x | D-β-homoPhe | D-Ala | L-Ala | L-Ala | L-Ala | L-Ala | 5 ± 1 |
| 2y | D-β-homoPhe | L-Phe | L-Ala | D-Ala | L-Ala | L-Ala | 8 ± 2 |
| FK506 | | | | | | | 0.22 ± 0.08 |
| Rapamycin | | | | | | | 0.057 ± 0.02 |
| SLF | | | | | | | 2.6 ± 1.5 |

[a]The IC$_{50}$ values reported were mean ± SD from multiple independent titration experiments (n) (rapalogs, n = 2-4; FK506, n = 5; rapamycin, n = 3; SLF, n = 18).

To facilitate solid-phase synthesis, an invariant glutamine was added to the C-terminal side of the R$^1$ residue, for the purpose of backbone peptide cyclization and providing an anchor for attachment to the solid support. For this set of compounds, the dipeptide Ala-Ala was used as the effector domain. The rapalogs were tested for binding to FKBP by a fluorescence polarization competition assay[22,23]. SLF[24], was labeled with the fluorescent dye fluorescein[23]. Binding of the labeled ligand to FKBP increases its fluorescence anisotropy (FA) values. Addition of an unlabeled ligand to the reaction inhibits the binding of SLF to FKBP and therefore decreases the FA values. By using this competition assay in the presence of increasing concentrations of the rapalogs, we determined the $IC_{50}$ values (concentration of peptide at which the FA value of SLF is reduced by 50%) for the rapalogs (Table 1). Subsequently, the $IC_{50}$ values were converted into $K_I$ values based on the Cheng-Prusoff equation. The $K_I$ values for some representing molecules are shown in Table 2.

ing crude peptides were quickly passed through a silica gel column to remove the salts and used directly in activity assays.

Figure 6:
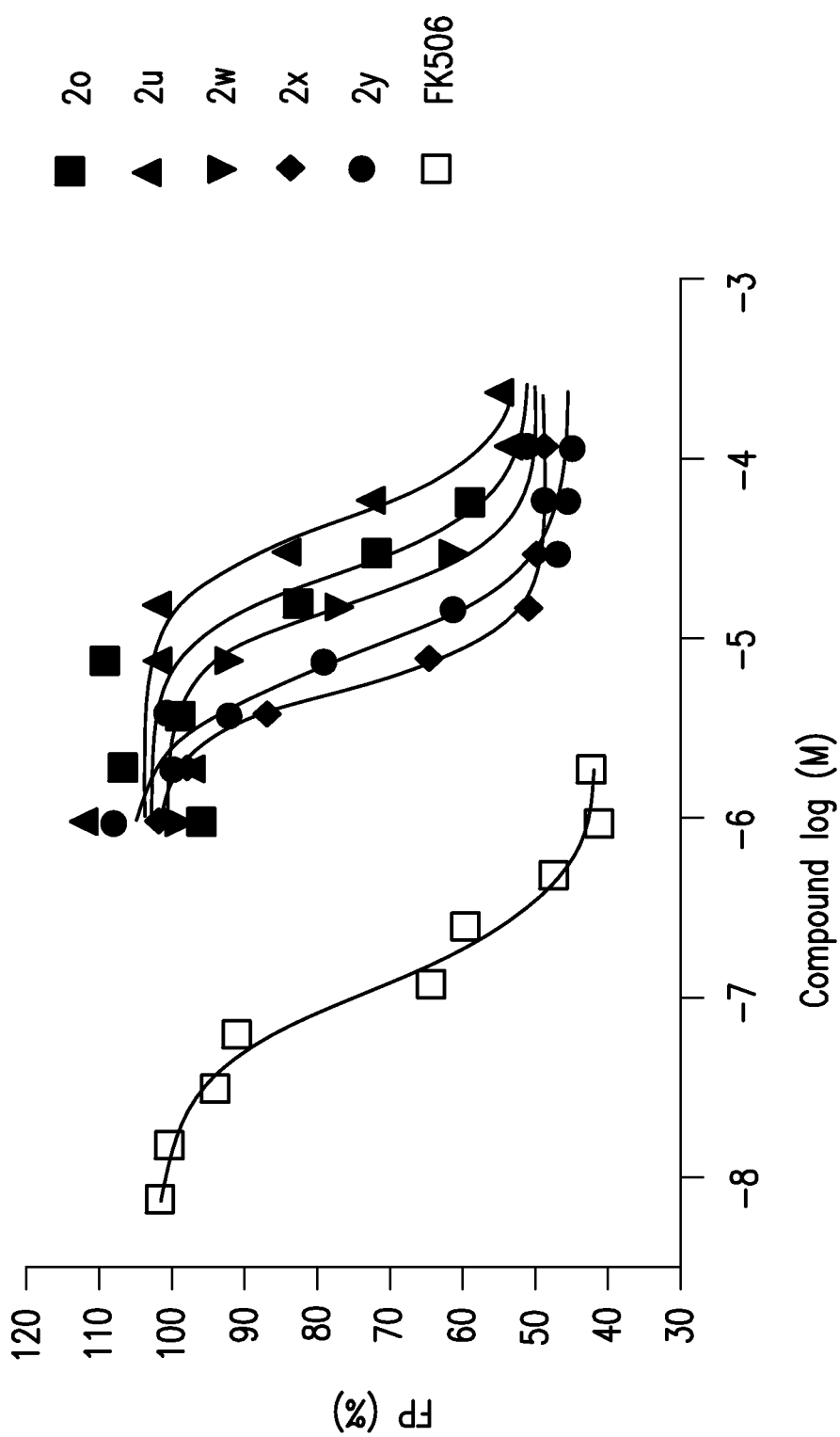
FIG. 6 shows representative titration curves showing the competition of FK506 or rapalogs 2o-2y (1-200 μM) with SLF-fluorescein (100 nM) for binding to FKBP (200 nM) as monitored by fluorescence anisotropy (FA). The percentage of FA was plotted against the rapalog concentration (in logarithmic scale).

Peptides 2a-n were tested for binding to FKBP by a fluorescence polarization competition assay[44,45]. A previously reported synthetic ligand of FKBP[46] (SLF in FIG. 2), was labeled with the fluorescent dye fluorescein[20]. Binding of the labeled ligand to FKBP increases its fluorescence anisotropy (FA) value. Addition of an unlabeled rapalog to the reaction inhibits the binding of SLF to FKBP and decreases the FA value (FIG. 6). By using this competition assay in the presence of increasing concentrations of the rapalogs 2a-n, we determined the $IC_{50}$ values (concentrations of rapalogs at which the FA value of SLF is reduced by 50%) for the peptides (Table 1).

TABLE 2

Binding affinities($K_I$ values) of various rapalogs, FK506 and rapamycin in the FA-based FKBP binding assay.

| Compound | Building Blocks | | | | | | Ki (µM) |
|---|---|---|---|---|---|---|---|
| | $R_1$ | $R_2$ | $R_3$ | $R_4$ | $R_5$ | $R_6$ | |
| 2a | L-Ala | D-Ala | L-Ala | L-Ala | | | 7 ± 1 |
| 2b | D-β-Glu | D-Ala | L-Ala | L-Ala | | | 9 ± 1 |
| 2c | L-β-homoPhe | L-Phe | L-Ala | L-Ala | | | 0.8 ± 0.1 |
| 2d | D-β-homoPhe | L-Phe | L-Ala | L-Ala | | | 0.5 ± 0.1 |
| 2e | D-β-homoPhe | D-Ala | D-Ala | D-Ala | | | 0.4 ± 0.1 |
| 2f | D-β-homoPhe | L-Thr | L-Ala | L-Ala | L-Ala | | 0.3 ± 0.1 |
| 2g | D-β-homoPhe | L-Phe | L-Ala | D-Ala | L-Ala | | 0.9 ± 0.2 |
| 2h | D-β-homoPhe | D-Ala | L-Ala | L-Ala | L-Ala | | 0.18 ± 0.06 |
| 2i | D-β-homoPhe | D-Ala | L-Ala | L-Ala | L-Ala | L-Ala | 0.15 ± 0.03 |
| FK506 | | | | | | | 0.007 ± 0.002 |
| Rapamycin | | | | | | | 0.002 ± 0.001 |

Synthesis of cyclic peptides 2a-n began with the preparation of a key building block 3 (FIG. 4). Starting from the commercially available N-Fmoc-L-pipecolinic acid, its carboxyl group was protected as an allyl ester by treatment with allyl bromide under basic conditions. Removal of the Fmoc group with piperidine gave amine 4, which was acylated with dihydro-4,4-dimethyl-2,3-furandione to give alcohol 5[43] (building block 3, amine 4, and alcohol 5, as well as other aspects of the synthesis are described in greater detail in the Examples, below). Coupling of alcohol 5 with three different N-Fmoc amino acids followed by allyl removal with Pd(PPh$_3$)$_4$ afforded the building block 3a-c in good yields (~45% overall).

Next, the 15 cyclic peptides were synthesized in parallel on Rink amide resin (FIG. 5). N-Fmoc-Glu-α-allyl ester was coupled to the amino group of Rink resin using O-benzotriazole-N,N,N',N'-tetramethyluronium hexafluorophosphate (HBTU) as the coupling agent. After removal of the Fmoc group, the N-terminal amine was acylated with the 10 different N-Fmoc amino acids ($R^1$) described above. Subsequent addition of building blocks 3a-c and L-Ala-L-Ala were carried out using standard peptide chemistry. Following the coupling of $R^1$ and $R^3$ residues, removal of the Fmoc groups with piperidine should be carried out quickly and the resulting amines should be immediately acylated with the next amino acid to avoid undesired cyclization at the ester moieties. Prior to peptide cyclization, the C-terminal allyl group was removed by treatment with a catalytic amount of Pd(PPh$_3$)$_4$ in the presence of N-methylaniline and the N-terminal Fmoc group was removed by piperidine. Peptide cyclization was achieved by using benzotriazole-1-yl-oxytripyrrolidinophosphonium hexafluorophosphate (PyBop) as the coupling reagent. Finally, treatment with 50% trifluoroacetic acid (TFA) in dichloromethane released the peptides from the resin and deprotected the amino acid side chains. The result- The results show that a D-β-homoPhe at the $R^1$ position resulted in the best binding affinity for FKBP ($IC_{50}$=4-18 µM) and L-β-homoPhe was slightly less effective ($IC_{50}$=26 µM), whereas the other eight building blocks were much less effective ($IC_{50}$≥147 µM) (Table 2). This is not surprising, since D-β-homoPhe is structurally similar to the 2-cyclohexylethyl-3-hydroxyketone moiety of rapamycin and the (R)-1-(phenylethyl)benzyl moiety in SLF and compound 1b (FIG. 2). Among the three $R^2$ residues examined, the smaller residues (L-Thr and D-Ala) were somewhat more effective than L-Phe (Table 1 compare compounds 2e, 2k, and 2n). Therefore, we chose the tetrapeptide L-Thr (or D-Ala)-Dkb-Pip-D-β-homoPhe as the minimal structural unit for binding to FKBP.

2. Effect of Ring Size and Building Blocks in the Effector Domain.

For the approach described herein to be successful, FKBP must be able to tolerate structurally diverse effector domains of different ring sizes and building blocks. As an initial test of the feasibility, additional rapalogs (e.g., compounds 2o-y, see Table 1) were synthesized, which all contain L-Thr (or D-Ala, L-Phe)-Dkb-Pip-D-3-homoPhe as the FKBP-binding domain but have zero to four L- or D-Ala residues as the effector domain. All of the compounds bound to FKBP with high affinity and the $K_I$ values were rather similar (0.15-1.1 µM, e.g. 2p and 2x (Table 1 and 2)). And, all of the compounds bound to FKBP with high affinity with $IC_{50}$ values in the range of 5-37 µM. In comparison, rapamycin, FK506, and SLF had $IC_{50}$ values of 0.057, 0.22, and 2.6 µM, respectively, under the same conditions (Table 1). These results suggest that FKBP can tolerate a wide variety of effector domains including different ring sizes and both L- and D-amino acids as building blocks.

3. Synthesis and Evaluation of a Pilot Rapalog Library.

To gain further insight into the SAR with respect to the influence of the effector domain structure on FKBP-binding activity, a 200-member rapalog library was synthesized on Rink amide resin in parallel by following a procedure similar to that described in FIG. 5. All of the compounds contained the tetrapeptide D-Ala-Dkb-Pip-D-β-homoPhe as the FKBP-binding domain. For half of the library members (Table 3, rapalog A series), a dipeptide of random sequence ($R^3$ and $R^4$) was employed as the effector domain, while a tripeptide ($R^3$—$R^4$-L-Ala) was used as the effector domain for the other half (rapalog B series in Table 3). At each random position ($R^3$ and $R^4$), 10 different amino acids (D-Thr, Gly, Ala, D-Val, Pro, Lys, Trp, Asp, D-Phe, and Nle) were used. After synthesis, side-chain deprotection, and cleavage from the resin, the rapalogs were analyzed by matrix-assisted laser desorption ionization-time of flight mass spectrometry (MALDI-TOF MS) and each showed a single species with the expected m/z value.

TABLE 3

Binding Affinities ($IC_{50}$, μM) of Pilot Rapalog Library Members to FKBP[a]

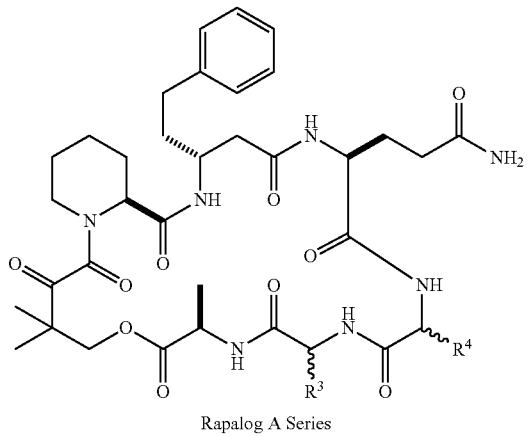

Rapalog A Series

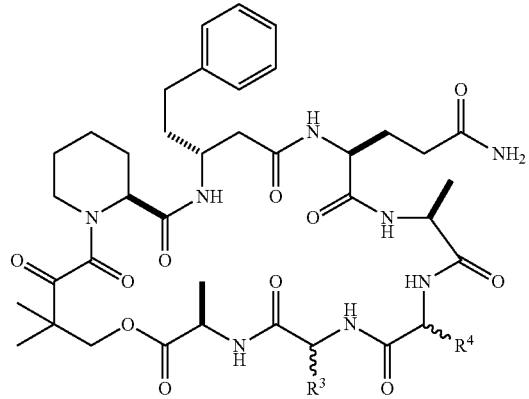

Rapalog B Series

11

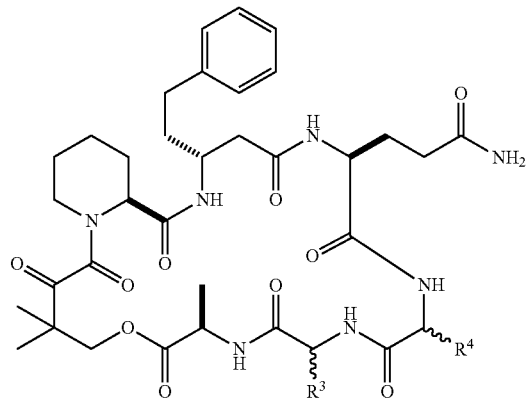

12

TABLE 3-continued

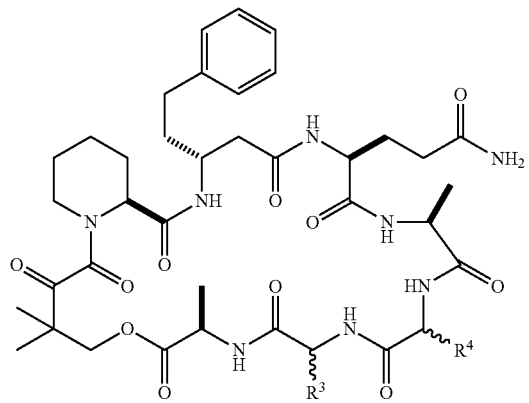

| R³ | R⁴ | D-Thr | Gly | Ala | D-Val | Pro | Lys | Trp | Asp | D-Phe | Nle |
|---|---|---|---|---|---|---|---|---|---|---|---|
| D-Thr | A | 17 ± 1 | 27 ± 2 | 15 ± 1 | 18 ± 5 | 19 ± 1 | >100 | 37 ± 10 | 12 ± 1 | 65 ± 4 | >100 |
|  | B | 5 ± 1 | 14 ± 4 | 4 ± 1 | ND | >100 | 80 ± 35 | 8 ± 3 | 25 ± 5 | 28 ± 2 | 57 ± 18 |
| Gly | A | 13 ± 5 | 25 ± 7 | ND | 25 ± 6 | 17 ± 1 | 30 ± 7 | 18 ± 4 | 24 ± 9 | 21 ± 6 | 32 ± 6 |
|  | B | 16 ± 2 | 26 ± 7 | 5 ± 2 | 70 ± 16 | 49 ± 12 | 5 ± 2 | 9 ± 1 | 10 ± 1 | 95 ± 25 | 38 ± 11 |
| Ala | A | 23 ± 4 | 28 ± 13 | ND | 14 ± 4 | >100 | 63 ± 11 | 9 ± 3 | 17 ± 6 | ND | 28 ± 9 |
|  | B | ND | 14 ± 5 | 6 ± 1 | 41 ± 4 | 57 ± 6 | >100 | 9 ± 3 | 8 ± 4 | 71 ± 17 |
| D-Val | A | 55 ± 5 | 5 ± 1 | 62 ± 2 | >100 | 12 ± 5 | 12 ± 4 | 9 ± 3 | 10 ± 1 | >100 | 48 ± 8 |
|  | B | 89 ± 16 | 2 ± 1 | 35 ± 6 | >100 | >100 | 52 ± 25 | 8 ± 2 | 13 ± 7 | >100 | 36 ± 17 |
| Pro | A | 41 ± 8 | ND | 33 ± 10 | 64 ± 10 | 27 ± 6 | 36 ± 8 | 21 ± 6 | 21 ± 2 | 46 ± 2 | 71 ± 15 |
|  | B | 38 ± 11 | 6 ± 3 | 21 ± 3 | 43 ± 1 | ND | 29 ± 5 | ND | 3 ± 1 | 87 ± 5 | 26 ± 7 |
| Lys | A | 62 ± 8 | 93 ± 31 | >100 | 80 ± 28 | 58 ± 10 | >100 | 12 ± 1 | 22 ± 4 | 47 ± 10 | 67 ± 10 |
|  | B | >100 | 22 ± 4 | >100 | ND | 15 ± 5 | 37 ± 6 | ND | 4 ± 1 | 45 ± 12 | >100 |
| Trp | A | 75 ± 16 | 12 ± 6 | 16 ± 2 | 34 ± 10 | 41 ± 9 | 53 ± 15 | 21 ± 04 | 8 ± 2 | ND | 13 ± 2 |
|  | B | 89 ± 12 | 14 ± 1 | 6 ± 1 | 15 ± 3 | 66 ± 2 | ND | 42 ± 10 | 15 ± 4 | 22 ± 1 | 44 ± 6 |
| Asp | A | 13 ± 2 | 7 ± 2 | 13 ± 4 | 11 ± 2 | 13 ± 1 | 10 ± 3 | 4 ± 1 | 19 ± 4 | 15 ± 1 | 5 ± 1 |
|  | B | 18 ± 5 | 12 ± 2 | 5 ± 2 | 50 ± 17 | 60 ± 4 | 7 ± 1 | 4 ± 2 | 2 ± 1 | 21 ± 6 | 10 ± 2 |
| D-Phe | A | 50 ± 16 | 40 ± 15 | 84 ± 24 | 38 ± 14 | 71 ± 23 | >100 | 69 ± 6 | 4 ± 1 | 34 ± 5 | ND |
|  | B | 81 ± 16 | 38 ± 6 | ND | 50 ± 11 | >100 | >100 | 6 ± 3 | 4 ± 1 | 35 ± 1 | ND |
| Nle | A | 72 ± 19 | 24 ± 5 | 31 ± 9 | 68 ± 12 | 13 ± 1 | >100 | 14 ± 1 | ND | 33 ± 5 | 28 ± 6 |
|  | B | >100 | 24 ± 6 | 35 ± 11 | 23 ± 13 | 79 ± 2 | 40 ± 11 | 11 ± 3 | 8 ± 1 | ND | 17 ± 2 |

*The IC$_{50}$ values reported were mean ± SD from 2-4 independent titration experiments.

The 200 compounds were individually assayed for their binding affinities to FKBP by the FA competition assay and their IC$_{50}$ values are listed in Table 3. Evaluation of the 200 compounds revealed several important trends. First, out of the 182 compounds whose IC$_{50}$ values were reliably determined, the great majority of them (163 compounds) bound to FKBP with excellent to respectable affinities (IC$_{50}$ of 2-93 µM). Some of the compounds were more potent than SLF and only ~10-fold less potent than FK506 (IC$_{50}$=0.22 µM). Second, although for a particular peptide sequence the two different ring sizes may result in as much as 10-fold difference in the IC$_{50}$ values, in general, the compounds from the two sublibraries of different ring sizes have similar potencies, consistent with our earlier observations. Third, at the R³ position, an Asp resulted in the most potent ligands against FKBP (IC$_{50}$=2.0-25 µM), whereas Lys generally gave poorer activities. Finally, the R⁴ residue had minimal effect on the binding affinity and all 10 amino acids were well tolerated. The only exception was Asp, which gave high activities for most compounds, even when the R³ residue was not optimal (e.g. when R³ was Lys).

To confirm the library screening results, which were carried out with crude samples, four of the rapalogs that had relatively high activities to FKBP were purified to homogeneity by HPLC (compounds A1, B1 (or 2p), B2, and B3 in Table 4). The pure samples were assayed for binding to FKBP under the same conditions to give IC$_{50}$ values of 6.3, 4.9, 7.0, and 6.3 µM, respectively (Table 4). These values were ≤2-fold different from those derived from the crude samples; these differences were well within the margin of error for the competition assay method.

TABLE 4

Comparison of the Binding Affinities of Crude vs. Purified Rapalogs to FKBP.

|  | Crude sample | | Purified sample | |
|---|---|---|---|---|
| Rapalog (R³, R⁴) | IC$_{50}$ (µM) | K$_I$ (µM) | IC$_{50}$ (µM) | K$_I$ (µM) |
| A1 (Asp, D-Phe) | 15 ± 1 | 0.48 ± 0.04 | 6.3 ± 1 | 0.20 ± 0.01 |
| B1 (2p) (Ala, Ala) | 6.0 ± 2.0 | 0.19 ± 0.03 | 4.9 ± 1.4 | 0.15 ± 0.04 |
| B2 (Asp, Ala) | 5.0 ± 2.0 | 0.16 ± 0.06 | 7.0 ± 2.1 | 0.22 ± 0.10 |
| B3 (Gly, Ala) | 4.7 ± 2.1 | 0.16 ± 0.06 | 6.3 ± 2.8 | 0.20 ± 0.09 |

*The IC$_{50}$ values reported were mean ± SD from 2-4 independent titration experiments.

Figure 7A:
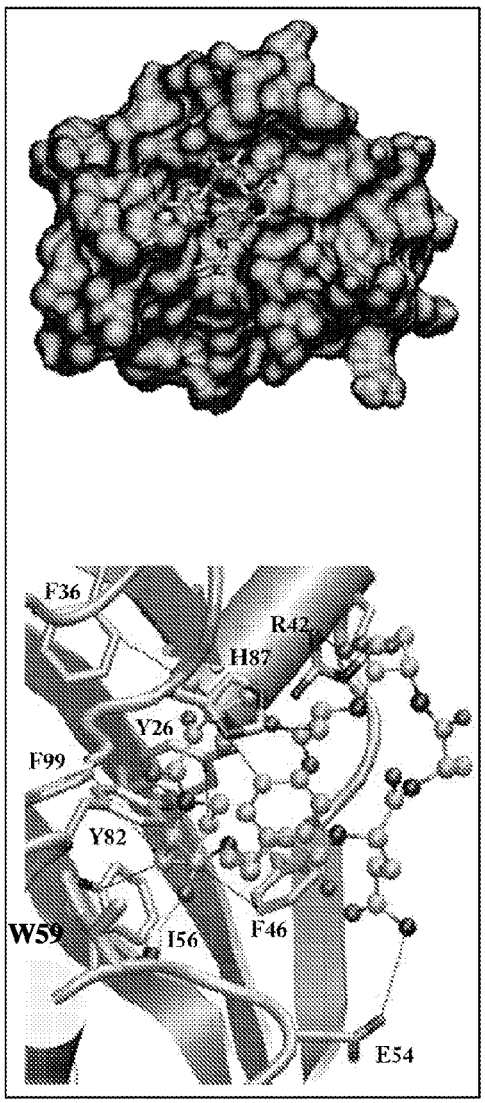
FIG. 7 shows top (a) and side view (b) of the overall FKBP-rapalog 11b complex. FKBP is rendered as a surface with a probe radius of 1.4 Å and rapalog is in a licorice representation with hydrogen atoms omitted for clarity. C, O and N atoms are colored in cyan, red, and blue, respectively. (c) Stereo view of the complex between FKBP (shown in silver color except for the O and N atoms involved in binding) and rapalog 11c [color scheme: C (cyan), O (red), and N (blue)]. Dash lines indicate intermolecular hydrogen bonding, electrostatic, and CH-π interactions between the rapalog and the active-site residues of FKBP.
Figure 7B:
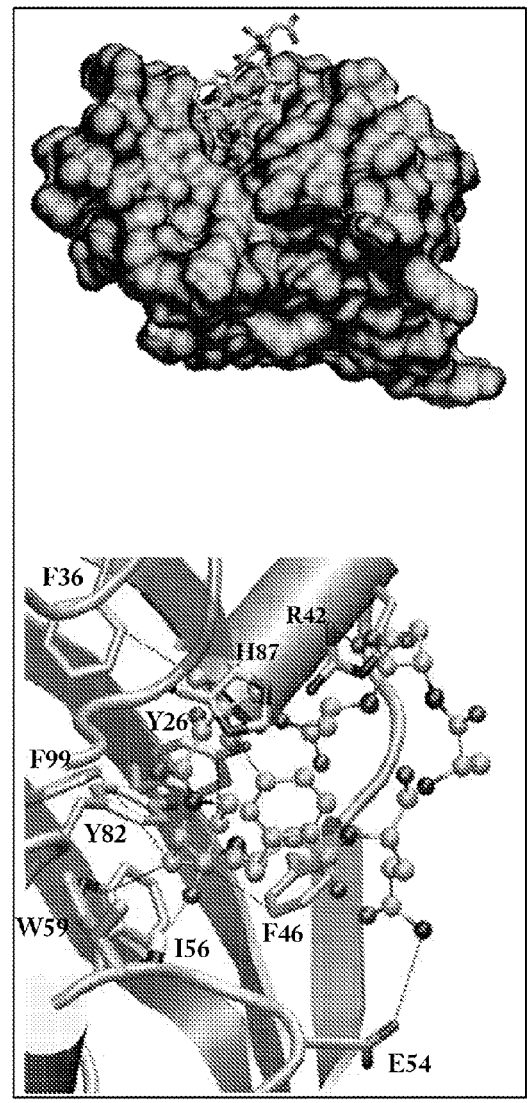

Molecular Modeling of the FKBP-Rapalog Complexes. To gain some structural insight into the above observed SAR, molecular modeling was carried out for the binding of FKBP to rapalogs B2(R³=Ala, R⁴=Asp) and B3(R³=Asp, R⁴=Ala) using a two stage protocol as described in the Example, below. In the model, the D-Ala-Dkb-Pip-D-β-homoPhe FKBP-binding motif is mostly buried in the active site, whereas the effector domain is largely exposed to the solvent (FIGS. 7a and b). A key FKBP-rapalog binding interaction occurs in the form of CH-π interactions between the side chain of Pip and the hydrophobic pocket formed by the side chains of Tyr-26, Phe-46, Trp-59, and Phe-99 of FKBP (FIG.

7c). The carbonyl groups of Dkb and Pip also make two key hydrogen bonds with the side chain of Tyr-82 and the main-chain —NH of Ile-56, respectively. The pro-(S) methyl group of Dkb makes hydrophobic contact with Phe-36 side chain, while its pro-(R) methyl group interacts with the side chain of His-87. In addition, the phenyl ring of D-β-homoPhe contacts the side chains of Tyr-82 and His-87. The side chain of the D-Ala ($R^2$) points away from the protein, consistent with the tolerance of different side chains at this position (e.g., D-Ala, Thr, and Phe). Some of the effector domain residues also contribute to the overall binding affinity. The side chain of Asp at position $R^3$ is physically proximal to and engages in charge-charge interaction with the guanidinium group of FKBP Arg-42 (FIG. 7c). A similar electrostatic interaction also occurs when an Asp or Glu is placed at the $R^4$ position (FIGS. 7a and b). This is in excellent agreement with our experimental observations (Table 3). Finally, the side chain amide of the anchoring Gln is 3.82 Å from the side chain of Glu-54, suggesting that they may be involved in electrostatic interactions as well. Overall, the modeled binding mode explains why FKBP is capable of binding to the wide variety of rapalogs in this work.

4. Design and Synthesis of a Large Rapalog Library (Rapalog C Series).

To generate a very large library of rapalog-FKBP chemobodies in an academic setting, the one-bead-one-compound (OBOC) screening approach was used. In OBOC screening (which is well known to those of ordinary skill in the art), each bead carries a distinct compound. If a bead is positive in a screen, the bead is isolated and the compound on the bead is identified by decoding a specific tag that is created on the bead in parallel to the synthesis of the compound. For the synthesis of the presently-described library, the tag is the corresponding linear peptide that constitutes the variable part of the rapalog on the bead.

A rapalog library was synthesized on 2 g of aminomethyl-ChemMatrix resin, which corresponds to ~6 million beads. A common linker BBRM (B=β-alanine) was first added to the resin (FIG. 8); this linker is important for peptide release (cleavage with CNBr after Met) and peptide sequencing by MS (Arg provides positive charge). At this point, each bead was spatially segregated into two layers, with a cyclic peptide displayed on the bead surface and the corresponding linear peptide in the bead interior. For simplicity and clarity of the figure, only the synthesis of the cyclic peptide portion is shown in FIG. 8.

To achieve the segregation, the beads were soaked in water, drained, and rapidly suspended in 0.5 equiv of Fmoc-Glu (NHS)—OAll, which has an N-succinimide ester on its side chain. This procedure results in the acylation of surface amines. The resin was then treated with excess Fmoc-Glu (tBu)-OH and HBTU, which acylate all of the remaining amines in the bead interior. Next, the resin was coupled to Fmoc-beta-homoPhe and building block 4 [which had been prepared with 5 different $R_1$ groups (D-Ala, Leu, Val, Phe, and D-Nle) in the solution phase] by using standard Fmoc chemistry. The random region was synthesized by split-and-pool synthesis[26,27] using standard Fmoc chemistry and 25 amino acid building blocks as previously described.[33,34] These building blocks included 11 proteinogenic L-amino acids (Ala, Gly, Ser, Pro, Ile, Gln, Glu, His, Arg, Tyr, Trp), 5 unnatural amino acids (L-ornithine (Orn), L-Phenylglycin (Phg), L-para-fluoro-phenylalanine (L-Phe(Fpa)), D-2-naphtylalanin (nal, D-norleucine (nle)) as well as 9 D-amino acids (D-Ala (a), D-Val (v), D-Pro (p), D-Thr (t), D-Leu (l), D-Asn (n), D-Lys (k), D-Phe (f), D-Asp (d)). This 25-amino acid set was chosen to give maximum structural diversity and protease resistance while minimizing the cost of production (all commercially available).

For peptide cyclization, the resin was treated with $Pd(PPh_3)_4$ to remove the allyl group from the C-terminal Glu and then with piperidine to remove the N-terminal Fmoc group. Subsequent treatment with PyBOP cyclized the 50% of the peptides on the bead surface, whereas the other 50% of the peptides (which contain a t-Bu protected C-terminal Glu) remains linear and can serve as the encoding tags for sequencing analysis. The library was deprotected with standard conditions (TFA and triisopropylsilane) and was ready for use (see FIG. 8 for schematic of synthesis)

Post screening, beads that contain rapalog "hits" are manually isolated and decoded by identifying the sequence of the linear peptide tag. An inexpensive, high-throughput peptide sequencing technique termed "partial Edman degradation/mass spectrometry (PED/MS)", which is ideally suited for sequencing resin-bound peptides[25] has been developed (as described in Thakkar, A., Wavreille, A. S. & Pei, D. Traceless capping agent for peptide sequencing by partial edman degradation and mass spectrometry. *Analytical Chemistry* 78, 5935-5939 (2006). incorporated by reference herein in its entirety). On a simple MALDI-TOF instrument, 20-30 beads can be sequenced in an hour at a low cost (e.g., $1/bead—cost of reagents and MS machine time), at a success rate of >90%.

5. Comparison with Previous Approach.

As described above, previous studies required a pre-existing ligand with high affinity and specificity to the target of interest; however, for many high-value targets such as the flat surfaces involved in protein-protein interactions, no such ligand is available (or possible). To recognize these flat surfaces, which are generally considered as "undruggable" by the conventional small-molecule approaches, the present application describes an alternative approach to recapitulate the mode of action of rapamycin and other natural products. The strategy is to generate a large library of bifunctional cyclic peptides, which contain a common FKBP-binding motif on one side and diverse effector domains on the other side. These cyclic peptides should bind to FKBP via their shared FKBP-binding motif to form a library of FKBP-cyclic peptide complexes, each of which displays a unique and relatively flat surface formed by both the FKBP protein and the variable face of the cyclic peptide. Screening of the library of composite surfaces against a target surface may then be used to identify complexes that can inhibit protein-protein interactions.

In the present application, it has been shown that the tetrapeptide D-Ala-Dkb-Pip-D-β-homoPhe acts as an effective minimal structural motif that binds to FKBP with high affinity and specificity. When the motif was incorporated into ~200 cyclic peptides of different ring sizes and amino acid building blocks, the vast majority of them (163 out of the 182 peptides tested) were capable of binding to FKBP with $IC_{50}$ values of 2-95 µM as determined by the FKBP competition assay, corresponding to $K_I$ values of 60-3000 nM (Tables 3 and 4). By using the same assay, a $K_I$ value of 7.0 nM was obtained for FK506, in reasonable agreement with the $K_I$ value of 1-2 nM previously reported for inhibition of FKBP rotamase activity by FK506.[43,50] Thus, the binding affinities of the rapalogs for FKBP are generally one to three orders of magnitude lower than that of FK506. Most importantly, the results as well as the previously reported examples[43,51,52] demonstrate that essentially any cyclic peptide or other types of macrocycles should be able to bind to FKBP, as long as they contain a FKBP-binding motif, such as the tetrapeptide identified herein, in a proper conformation.

6. Potential Applications.

There are at least two important applications for the above rapalog libraries. First, the rapalog-FKBP composite surfaces may be screened for inhibition of protein-protein interactions. As described above, protein-protein interaction is ubiquitous in biology and provides an exciting class of largely unexploited drug targets.[53] Unlike the conventional small-molecule drug targets, which typically contain deep pockets or clefts to make three-dimensional interactions with the small-molecule drugs, protein-protein interaction often involves large, flat surfaces, which are challenging targets for traditional small molecules. As has been repeatedly demonstrated in nature, the drug-protein composite surfaces are flat and sufficiently large in areas and should be able to bind to the flat surfaces involved in protein-protein interactions.

Second, the rapalog-FKBP composite surfaces may be utilized for isoform-specific inhibition of proteins and enzymes that belong to large families of structurally similar proteins such as protein kinases and protein tyrosine phosphatases (PTPs). The human genome encodes 500 protein kinases and ~100 PTPs.[54,55] Each enzyme family has a highly conserved active site, making it difficult to develop specific inhibitors against a particular kinase or PTP. Indeed, most of the kinase inhibitors so far designed target the ATP-binding site. But because the ATP-binding site is conserved, few of these inhibitors are truly selective for the intended kinase target. For the same reason, few selective PTP inhibitors are currently available. On the other hand, for both kinases and PTPs, the protein surfaces outside the active site are highly divergent. It is conceivable to design or screen for a rapalog-FKBP composite surface that recognizes a unique surface area outside (but near) the kinase/PTP active site. While binding to such a site by a conventional small molecule may not have significant effect on the biological activity of the enzymes, association with a rapalog-FKBP complex would create a steric block to the active site, preventing the access of kinase/PTP substrates, which are large protein molecules. This is precisely the mechanism by which FK506 and cyclosporin A inhibit the serine/threonine phosphatase calcineurin.[34]

The various aspects of the present invention will be described in greater detail with respect to the following non-limiting Examples.

E. EXAMPLES

1. Example 1

Creation and Evaluation of a Pilot Rapalog Library

FK506 and rapamycin are immunosuppressive drugs with a unique mode of action. Prior to binding to their protein targets, these drugs form a complex with an endogenous chaperone FK506-binding protein 12 (FKBP). The resulting composite FK506-FKBP and rapamycin-FKBP binding surfaces recognize the relatively flat target surfaces of calcineurin and mTOR, respectively, with high affinity and specificity. To test whether this mode of action may be generalized to inhibit other protein targets, especially those that are challenging to inhibit by conventional small molecules, we have developed a parallel synthesis method to generate a 200-member library of bifunctional cyclic peptides as FK506 and rapamycin analogues, which were referred to as "rapalogs". Each rapalog consists of a common FKBP-binding moiety and a variable effector domain. The rapalogs were tested for binding to FKBP by a fluorescence polarization competition assay. Our results show that FKBP binds to most of the rapalogs with high affinity (KI values in the nanomolar to low micromolar range), creating a large repertoire of composite surfaces for potential recognition of macromolecular targets such as proteins.

a. Materials.

N-Fmoc amino acids were purchased from Advanced ChemTech (Louisville, Ky.), Peptides International (Louisville, Ky.), or NovaBiochem (La Jolla, Calif.). HBTU and 1-hydroxybenzotriazole hydrate (HOBt) were from Peptides International. TFA was purchased from Sigma-Aldrich. Dihydro-4,4-dimethyl-2,3-furandione, tetrakis(triphenylphosphine)palladium, allyl bromide, cesium carbonate and solvents were purchased from Aldrich, Fisher Scientific (Pittsburgh, Pa.), or VWR (West Chester, Pa.). Rink resin (0.20 mmol/g, 100-200 m) was purchased from Advanced ChemTech. $^1$H and $^{13}$C NMR spectra were recorded on a 400 μMHz spectrometer (operated at 400 and 100 μMHz, respectively). Chemical shifts are reported as δ values (ppm). NMR data were collected by using DMSO-$d_6$ or $CDCl_3$ as solvent. Reaction progress in solution phase was monitored by thin-layer chromatography (TLC), using 0.25 mm silica gel plates with visualization by irradiation with a UV lamp. Reaction progress in solid phase was monitored by ninhydrin test, whenever possible. HRMS data were collected with electrospray ionization mass spectrometry or direct probe ionization. MALDI-TOF mass analysis was performed on a Bruker III MALDI-TOF instrument in an automated manner at Campus Chemical Instrument Center of The Ohio State University. The data obtained were analyzed by either Moverz software (Proteometrics LLC, Winnipeg, Canada) or Bruker Daltonics flexAnalysis 2.4 (Bruker Daltonic GmbH, Germany). Flash column chromatography was carried out on silica gel 40.

b. Allyl $N^4$-Fluorenyloxycarbonyl-L-Pipecolate.

To a solution of 1.0 equiv of Fmoc-L-pipecolinic acid (0.5 mmol, 176 mg), dissolved in 10 mL of acetone (saturated by $K_2CO_3$), 2 equiv of $Cs_2CO_3$ (1 mmol, 326 mg) and 5 equiv allyl bromide (2.5 mmol, 302 mg) were added. The solution was stirred for 4 h at room temperature. The crude product was purified by using flash column chromatography on a silica gel column with hexane/ethyl acetate (2:1) as eluent to give a clear oil (yield 99%): $^1$H NMR (400 μMHz $CDCl_3$) δ1.30-1.74 (m, 6H), 2.30 (t, 1H), 3.10 (dt, 1H), 4.12 (t, 1H), 4.33 (m, 3H), 4.60 (dd, 2H), 5.30 (dd, 2H), 5.95 (m, 1H), 7.28-7.81 (m, 8H). $^{13}$C NMR (100 μMHz, $CDCl_3$) δ 171.3, 156.5, 144.1, 141.3, 131.8, 127.7, 127.1, 125.1, 120.0, 118.6, 67.7, 65.7, 54.5, 47.3, 41.8, 26.9, 24.7, 20.7. HRMS (ESI): calcd for $C_{24}H_{25}NO_4Na$ (M+Na+) 414.1682. found 414.1697.

c. Allyl-L-Pipecolinate (4).

Allyl $N^\alpha$-fluorenyloxycarbonyl-L-pipecolate was added to 20% piperidine in DCM solution. The solution is stirred for 20-25 min at room temperature and monitored by TLC. After evaporation of solvent, the crude product was purified by flash chromatography on a silica gel column eluted with hexane/ethyl acetate/EtOH/diisopropylethylamine (40:40:19:1) (80% yield). $^1$H NMR (400 μMHz CDCl$_3$) δ 1.42-2.01 (m, 6H), 2.64 (t, 1H), 3.05 (d, 1H), 3.45 (dd, 1H), 4.59 (dd, 2H), 5.25 (dd, 2H), 5.89 (m, 1H). $^{13}$C NMR (100 μMHz, CDCl$_3$) δ 171.2, 132.0, 118.4, 65.2, 58.6, 45.7, 29.2, 25.6, 24.1. HRMS: (ESI): calcd for C$_9$H$_{15}$NO$_2$ (M+H+) 170.1171. found 170.1181.

d. Allyl N$^4$-(3,3-dimethyl-4-hydroxy-2-ketobutyryl)-L-pipecolinate (5).

To a solution of amine 4 (0.33 mmol, 55 mg) dissolved in 1.5 mL of toluene was added dihydro-4,4-dimethyl-2,3-furandione (0.49 mmol, 62 mg) and 4-dimethylaminopyridine (DMAP) (0.033 mmol, 4 mg). The solution was stirred for 17-20 h at reflux temperature under argon atmosphere. After removal of solvent, the crude product was purified by flash chromatography on a silica gel column with hexane/ethyl acetate (2:1) as eluent (81% yield). $^1$H NMR (400 μMHz CDCl$_3$) δ 1.50 (s, 6H), 1.23-1.80 (m, 6H), 3.22 (dt. 1H), 3.50 (d, 1H), 3.56 (q, 1H), 4.44 (s, 2H), 4.66 (dd, 2H), 5.30 (dd, 2H), 5.90 (m, 1H). $^{13}$C NMR (100 μMHz, CDCl$_3$): δ 205.9, 170.1, 168.1, 131.4, 119.3, 69.3, 66.2, 51.6, 49.5, 44.2, 26.3, 24.8, 21.3, 20.9. HRMS (ESI) calcd for C$_{15}$H$_{23}$NO$_5$Na (M+Na+) 320.1474. found 320.1476.

e. Building Block 3.

To a solution of allyl ester 5 (1.0 mmol) in freshly distilled DCM (3 mL) was added the proper Fmoc-amino acid (1.05 mmol), N,N'-diisopropyl carbodiimide (2.0 mmol), and DMAP (0.05 mmol). The resulting mixture was stirred for 1 h at room temperature. The crude allyl ester products were purified by silica gel column chromatography using hexane/ethyl acetate (3:1) as eluent (90-95% yield). Next, the allyl ester (0.9 mmol) was dissolved in 4 mL of distilled THF, and Pd(Ph$_3$P)$_4$ (0.045 mmol) and N-methylaniline (2.7 mmol) were added. The solution was stirred for 40 min at room temperature under argon atmosphere and the color of the solution changed from light yellow to brown. The crude products were purified by flash silica gel column chromatography using hexane/ethyl acetate/AcOH (66:33:1) as eluent (70-80% yields).

3a. $^1$H NMR (400 μMHz CDCl$_3$) δ1.27 (s, 6H), 1.32 (d, 3H), 1.24-1.59 (m, 6H), 2.97 (m, 1H), 3.26 (m, 1H), 3.37 (m, 1H), 4.22-4.39 (m, 6H), 7.28-7.65 (m, 8H). $^{13}$C NMR (100 μMHz, CDCl$_3$) δ206.1, 203.5, 178.3, 172.5, 170.0, 163.3 157.0, 143.8, 141.3, 135.1, 132.2, 128.6, 127.8, 127.4, 125.1, 120.0, 70.0, 67.8, 67.1, 47.1, 46.6, 42.4, 41.6, 38.9, 30.9, 19.2. HRMS (ESI) calcd for C$_{30}$H$_{34}$N$_2$O$_8$Na (M+Na+) 573.2213. found 573.2216.

3b. $^1$H NMR (400 μMHz CDCl$_3$) δ 1.16-1.65 (m, 6H), 1.34 (s, 6H), 2.90 (s, 2H), 3.00 (m, 1H), 3.30 (m, 1H), 3.36 (m, 1H), 4.16-446 (m, 6H), 7.10-7.78 (m, 13H). $^{13}$C NMR (100 μMHz, CDCl$_3$) δ205.0, 204.0, 174.1, 172.0, 170.4, 166.3, 158.0, 156.8, 143.7, 141.3, 137.8, 128.6, 127.8, 127.2, 125.1, 120.0, 118.3, 74.1, 70.0, 67.8, 67.1, 47.1, 46.6, 42.4, 40.6, 38.9, 30.9, 19.3. HRMS (ESI) calcd for C$_{36}$H$_{38}$N$_2$O$_8$Na (M+Na+) 649.2526. found 649.2529.

3c. $^1$H NMR (400 μMHz CDCl$_3$) δ 1.14 (s, 9H), 1.17 (s, 3H), 1.47 (s, 6H), 1.23-1.79 (m, 6H), 3.10 (m, 1H), 3.30 (m, 1H), 3.51 (m, 1H), 4.01-4.59 (m, 7H), 5.30 (bs, 1H), 7.19-7.80 (m, 8H). $^{13}$C NMR (100 μMHz, CDCl$_3$) δ 205.2, 204.4, 174.0, 172.4, 170.4, 166.3, 158.0, 156.8, 143.7, 141.3, 137.8, 128.6, 127.8, 127.2, 125.1, 120.0, 118.3, 74.1, 70.0, 67.8, 59.0, 56.2, 47.1, 43.3, 33.3, 28.3, 27.3, 24.0, 20.0. HRMS (ESI) calcd for C$_{35}$H$_{44}$N$_2$O$_9$Na (M+Na+) 659.2944. found 659.2941.

f. Synthesis of Pilot Rapalog Library.

The library was synthesized on 0.50 g of Rink resin (0.20 mmol/g, 100-200 μm). Standard Fmoc/HBTU peptide chemistry was employed for all of the synthesis steps unless otherwise noted. The coupling reactions typically employed 2 equiv of Fmoc-amino acids, 2 equiv HBTU, 2 equiv HOBt and 4 equiv NMM for 2 h and were monitored by Ninhydrin tests. The Fmoc group was removed by treatment with 20% piperidine in DMF for 5-25 min. After each step, the beads were exhaustively washed with DMF and DCM. Starting from the Fmoc-protected rink resin, the Fmoc group was removed with piperidine and the exposed amine was acylated with N-Fmoc-Glu-α-allyl ester (2 equiv), followed by the coupling of Fmoc-D-β-homoPhe (2 equiv). The resin was treated with 20% piperidine for 5 min, exhaustively washed with DMF, and immediately coupled to building block 3a (1.5 equiv). The resulting resin was split into 10 equal aliquots and each aliquot was coupled to a different Fmoc-amino acid (D-Thr, Gly, Ala, D-Val, Pro, Lys, Trp, Asp, D-Phe, and Nle). After the coupling reaction was complete, each aliquot was further split into ten equal portions to give 100 individual samples. Each portion (5 mg) was individually treated with 20% piperidine (5 min) to remove the Fmoc group, washed exhaustively, and immediately coupled to one of the ten Fmoc-amino acids described above. At this point, each of the 100 samples was split into two equal portions. The first half was washed and stored for later cyclization to produce the rapalog A series, while the second half was subjected to another round of coupling reaction (to Fmoc-L-Ala) to expand the ring size of the cyclic peptides (rapalog B series). Prior to cyclization, the C-terminal allyl group was removed by treatment with Pd(PPh$_3$)$_4$ (0.2 equiv) and N-methylaniline (9.0 equiv) in anhydrous THF (45 min). The resin was washed sequentially with THF, DMF and DCM, and treated with 20% piperidine to remove the N-terminal Fmoc group. For peptide cyclization, the resin was suspended in a solution of PyBOP/HOBt/NMM (5, 5, and 10 equiv, respectively) in DMF and the mixture was incubated on a carousel shaker for 17-20 h. The cyclization reaction was terminated when ninhydrin tests showed negative results. The resulting resin was washed with DMF and DCM, dried under vacuum, and stored at 4° C. Cleavage of the peptides from the resin and side-chain deprotection was achieved by treating the resin with 50% trifluoroacetic acid in DCM for 1.5 h. The solvents were evaporated under vacuum and the crude peptides were dissolved in DCM containing 10% diethylpropylamine. The solution was quickly passed through a silica gel column to remove the salts, evaporated to dryness, and stored at 4° C. until use. Compounds 2a-y were prepared in a similar manner.

g. Evaluation of the Rapalog Library A and B Series.

To check the quality of library synthesis, each of the compounds from above (2a-y, sublibrary A series, and sublibrary B series) was dissolved in 0.1% TFA (in water) and analyzed by ESI or MALDI-TOF MS. Most of the compounds showed single species of the expected m/z ratios. Four of the compounds were selected for further purification by HPLC on a semi-preparative C-18 column, which was eluted by a linear gradient of 0-100% CH$_3$CN in water (containing 0.05% trifluoroacetic acid) over 20 min. The pure samples were assayed against FKBP and compared to the results obtained with the crude samples (Table 4). For activity assay, the samples were evaporated to dryness and redissolved in appropriate volumes of DMSO.

h. FKBP Binding Assay.

The fluorescence polarization based competition assay was performed in a 384-well plate. Each reaction (20 μL total volume) contained 137 mM NaCl, 2.7 mM KCl, 10 mM Na$_2$HPO$_4$, 1.76 mM KH2PO4, pH 7.4, 200 nM recombinant FKBP, 100 nM fluorescent probe FLU-SLF (kindly provided by I. Graef of Stanford University), and varying concentrations of rapalogs (0-5000 µM). After the addition of the rapalogs as the last component, the binding reactions were incubated for 1 h at room temperature to reach binding equilibrium. Anisotropy values were measured on a FlexStation 3 plate reader (Molecular Devices, Sunnyvale, Calif.). K$_I$ values were calculated from the corresponding IC$_{50}$ values using the method by Cheng-Prusoff[56] [K$_I$=IC$_{50}$/(1+D/K$_{DF}$)], where D is the concentration of FLU-SLF (100 nM) and K$_{DF}$ is the binding affinity of FLU-SLF for FKBP (3.3 nM).[20]

i. Molecular Modeling.

At the first stage, three dimensional structures were generated for rapalogs B1 and B2 by geometry optimization with the SPARTAN 02 program. Since the rapalogs have similar FKBP-binding motif to compound 13 of Holt et al.,[43] the coordinates for atoms in the binding motif were modeled using the coordinates of compound 13 in a 2.2-Å resolution x-ray crystal structure of its complex with FKBP. The binding motif was then fused with the cyclic peptide sequences of rapalogs B1 and B2 at both ends to generate an initial geometry. The latter was optimized at the HF/6-31+G* level with the geometry of the binding motif fixed. The optimized structure appears to be quite rigid, due to the formation of multiple hydrogen bonds between backbone amide —NH and carbonyl oxygens, as in antiparallel β-strands. During the second stage, the optimized rapalog structure was docked with FKBP by means of quantum mechanics/molecular mechanics (QM/MM) optimization to form the FKBP-rapalog complex. Initially, the rapalog was placed into the binding site of FKBP utilizing the crystal structure of a previously reported FKBP-rapalog complex[43] (PDB access number 1FKI) as a template. The QM layer contained the rapalog and the protein residues that directly interact with the rapalog, and was treated at the PM3 level. The MM layer included the rest of the FKBP protein and was described by the AMBER force field. The QM/MM optimization was performed using the Gaussian 03 package.[57] The QM/MM two-layer partitioning was performed as previously described.[58]

2. Example 2

Discovery of a K-Ras Inhibitor

Figure 9:
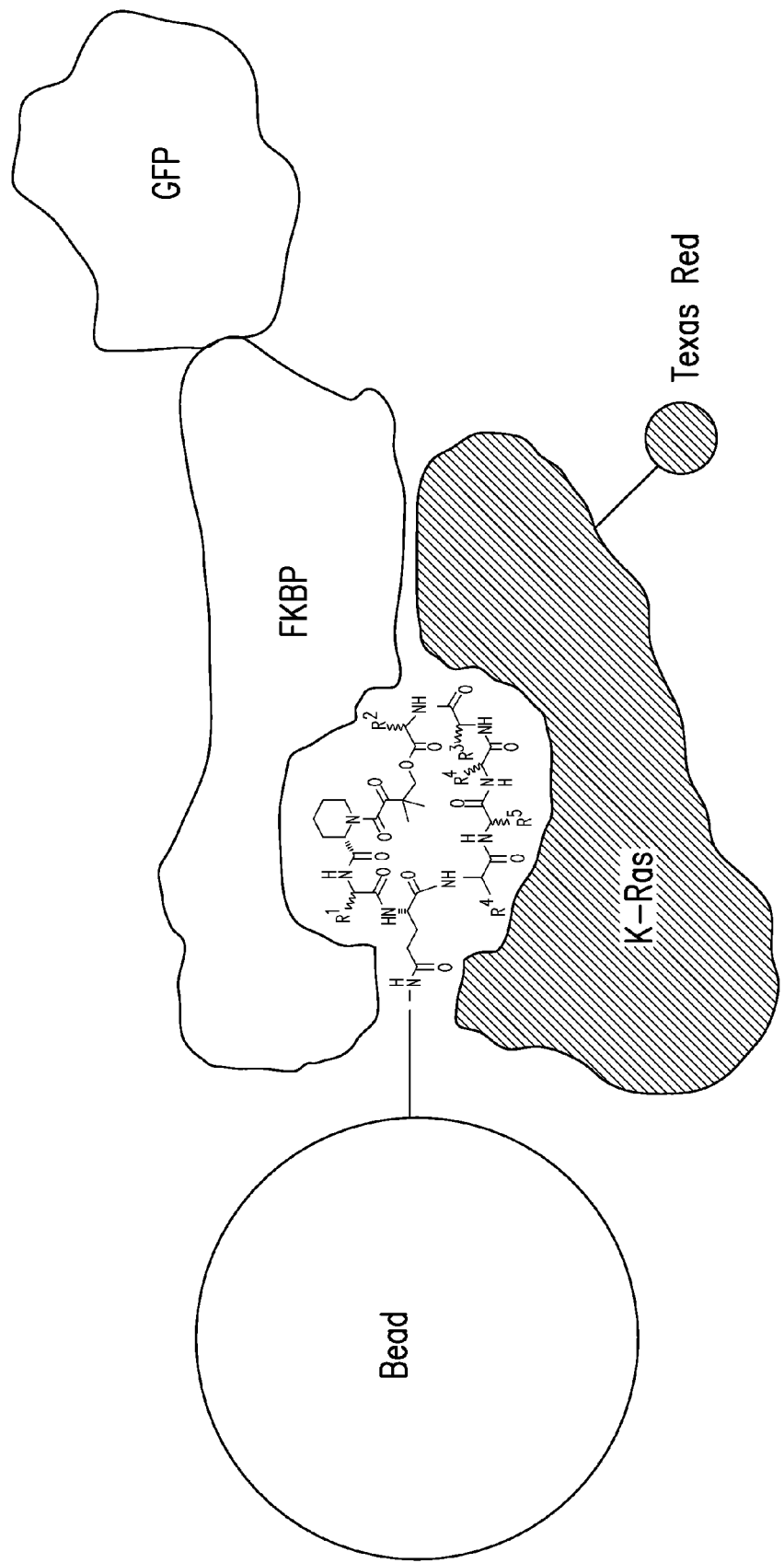
FIG. 9 shows the on-bead screening strategy in which fluorescently labeled FKBP (e.g. a FKBP-Green Fluorescent Protein fusion) and fluorescently labeled K-Ras (e.g. K-Ras G12V-Texas Red) are incubated with beads that present rapalogs on their surface.

Screen of the Large Rapalog Library (Rapalog C Series) against G12V K-Ras. Recombinant GST-K-Ras(G12V) was chemically labeled with the fluorescent dye Texas Red on a lysine residue. Since GST is larger and contains many more Lys than K-Ras, the dye should be mostly on GST and thus not affect the function of K-Ras. The library beads (~1,000,000 beads) were incubated in the presence of fluorescently labeled GST-K-Ras and recombinant FKBP fused to EGFP (enhanced green fluorescent protein) (~500 nM each). Under a fluorescent microscope, we found that a small number of the beads had both green and red fluorescence, indicating that they had bound both GST-K-Ras and FKBP-EGFP (FIG. 9).

The top 20 "hits" (ones with most intense red and green fluorescence) were isolated and sequenced by PED/MS.[25] Many of the selected rapalogs contained a pair of aromatic amino acids, often adjacent to each other (Table 5). Furthermore, the presence of positively charged amino acids was significant.

TABLE 5

Sequences of Selected Rapalogs C Series*

Rapalog C series

| Compd # | R1  | R2  | R3  | R4 | R5  | R6  |
|---------|-----|-----|-----|----|-----|-----|
| C1      | V   | n   | R   | R  | Fpa | Y   |
| C2      | nle | nal | nal | k  | R   | Fpa |
| C3      | F   | W   | k   |    |     |     |
| C4      | F   | R   | G   | Y  | nal | Orn |
| C5      | L   | R   | R   | Y  | Fpa | R   |
| C6      | F   | R   | Y   | P  | Y   | f   |
| C7      | F   | Phg | Fpa | R  | A   |     |
| C8      | T   | nal | a   | R  | Y   | R   |
| C9      | V   | Phg | t   | P  | E   | I   |
| C10     | F   | R   | S   | Y  | k   |     |
| C11     | L   | E   | Phg | f  | Orn | P   |
| C12     | nle | Fpa | R   | nal| R   | R   |
| C13     | F   | R   | nal | R  | f   | R   |
| C14     | L   | nal | R   | v  | R   | A   |
| C15     | F   | A   | Y   | R  | t   | G   |
| C16     | a   | Orn | v   | G  | nal | R   |
| C17     | F   | R   | Y   | R  | nal | R   |
| C18     | a   | R   | Fpa | W  | Phg | S   |
| C19     | a   | nal | nal | R  | H   | Y   |
| C20     | F   | nal | R   | Phg| S   | G   |

*Lowercase letters indicate D-amino acids.

Figure 10:
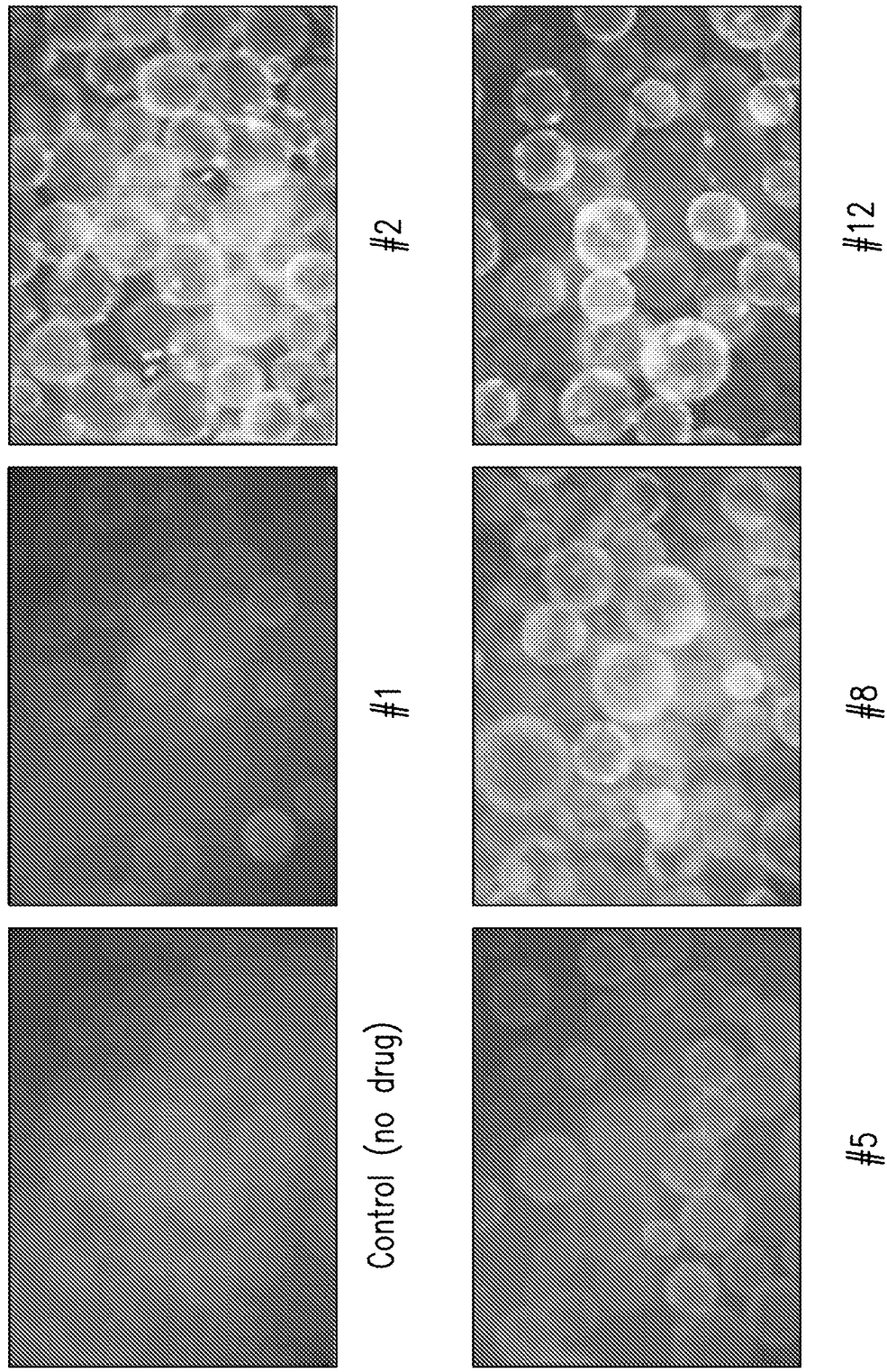
FIG. 10 shows that rapalogs identified in the K-Ras screen can promote binding of fluorescently labeled K-Ras G12V to beads on which FKBP is immobilized.

Fifteen of the hits listed in Table 5(C1-C15) were individually resynthesized on a larger scale (~10 mg). The compounds were tested for their ability to induce the binding between FKBP and K-Ras G12V. For this, we incubated glutathione beads that had bound GST-FKBP with red fluorescent Alexa 546-labeled G12V K-Ras (50 nM) and in the presence and absence of the rapalogs (100 □M). As shown in FIG. 10, K-Ras does not bind to the immobilized FKBP in the absence of rapalogs. However, almost all of the rapalogs induced binding of K-Ras to the GST-FKBP beads, with a few examples shown in FIG. 10.

Figure 11:
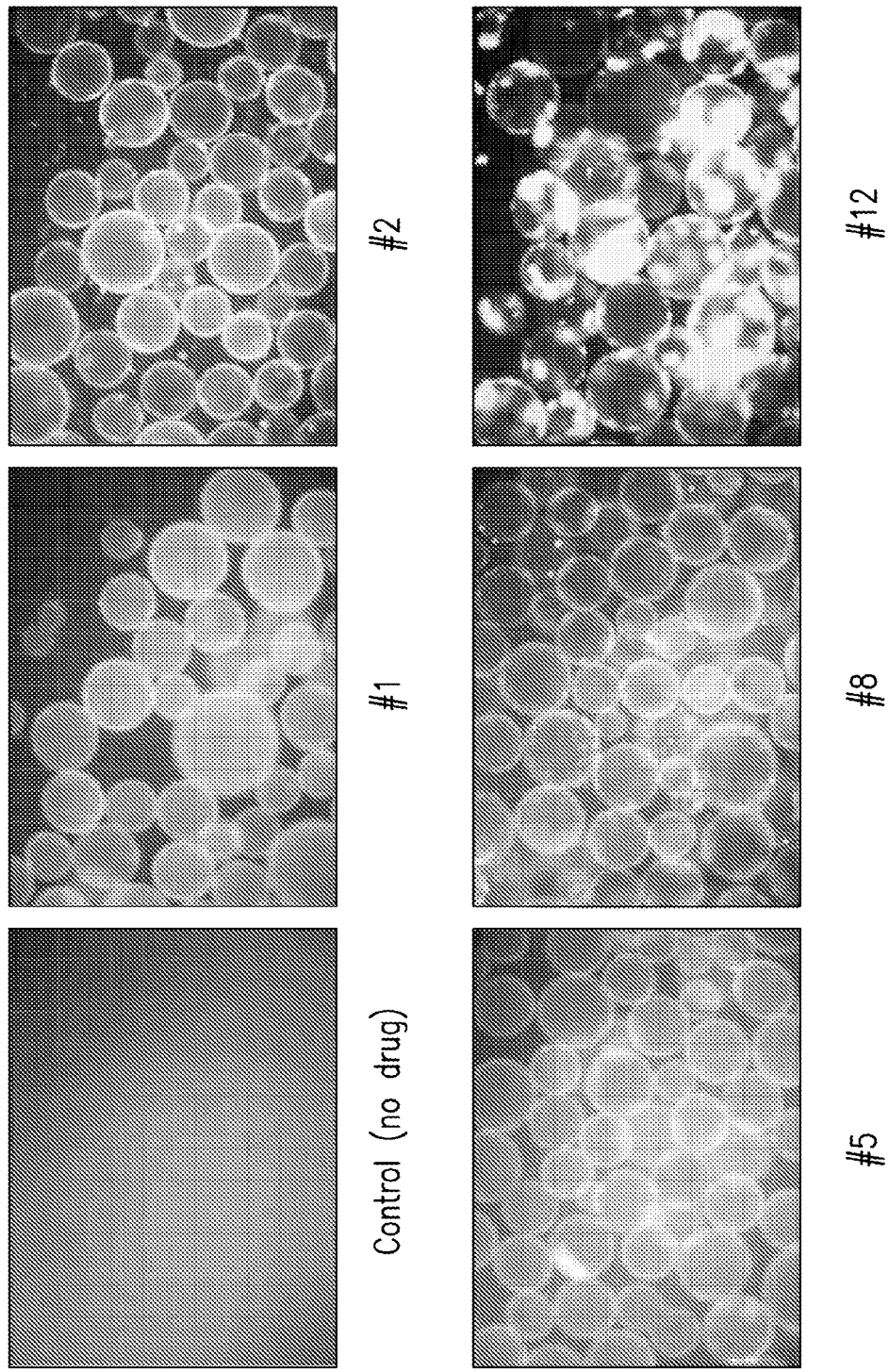
FIG. 11 shows that rapalogs identified in the K-Ras screen can promote binding of fluorescently labeled FKBP to beads that on which K-Ras G12V is immobilized.

The rapalogs were also tested for binding in the reverse direction by inducing binding of FKBP-EGFP to beads with immobilized GST-K-Ras(G12V). Again, almost all rapalogs resulted in green fluorescence on the beads (with some examples shown in FIG. 11). These results demonstrate that the selected rapalogs indeed form heterotrimeric complexes with FKBP and K-Ras.

Figure 12:
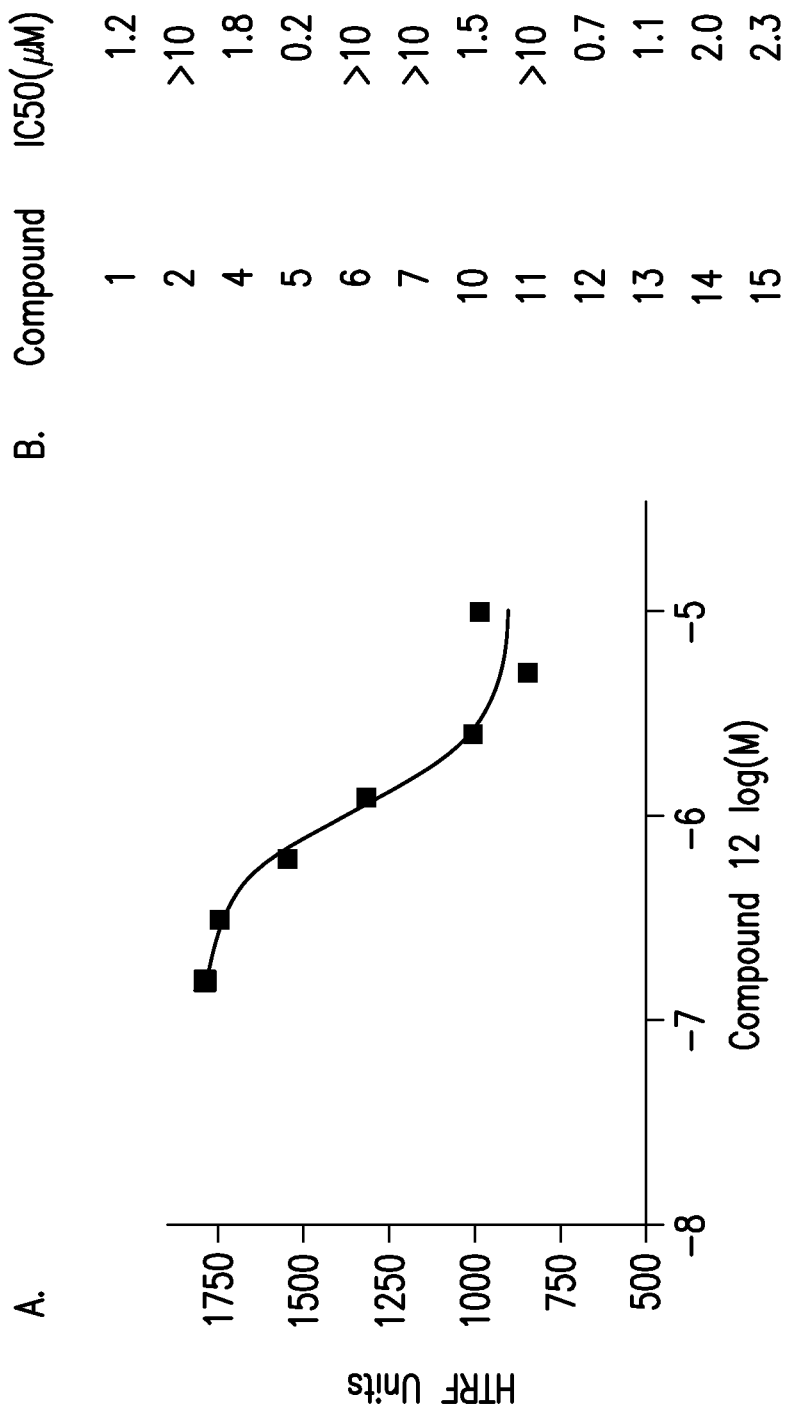
FIG. 12 Evaluating the activity of K-Ras hits to disrupt the interaction between K-Ras (G12V)-HA and GST-Raf RBD using an HTRF assay. A) A representative titration curve with compound #12. B) Table of IC50 values for various hits in the HTRF Ras-Raf inhibition assay.

Next, rapalogs C1-C15 were purified to homogeneity by HPLC and tested for their ability to inhibit the K-Ras-Raf interaction. Raf is an important K-Ras effector protein that activates the MAPK pathway. The homogeneous time-resolved fluorescence (HTRF) assay[101] was selected for this purpose. The Ras binding domain of Raf (GST-RBD) was incubated with HA-tagged G12V K-Ras. Fluorescently labeled anti-GST and anti-HA antibodies were added to the solution. The binding between GST-RBD and K-Ras brings the anti-GST and anti-HA antibodies into proximity, which can be detected by the HTRF measurement. Increasing concentrations of the purified rapalogs was then titrated into this solution and a decrease in HTRF signal was observed for most compounds. A plot of the HTRF signal against rapalog concentration produces a titration curve, from which the $IC_{50}$ value was estimated (FIG. 12). Compounds C5 and C12 were most potent in this assay ($IC_{50}$ of 200 and 700 nM, respectively).

Compound C12 was next labeled with fluorescent dye FITC and assayed for its binding affinity to K-Ras(G12V) and FKBP (no GST) by fluorescence polarization and a $K_D$ value of 830 nM was obtained. C12 also bound FKBP with a $K_D$ of 0.5 µM. Thus, compound C12 is a bifunctional molecule, capable of binding to K-Ras independent of FKBP and FKBP independent of K-Ras.

Figure 13:
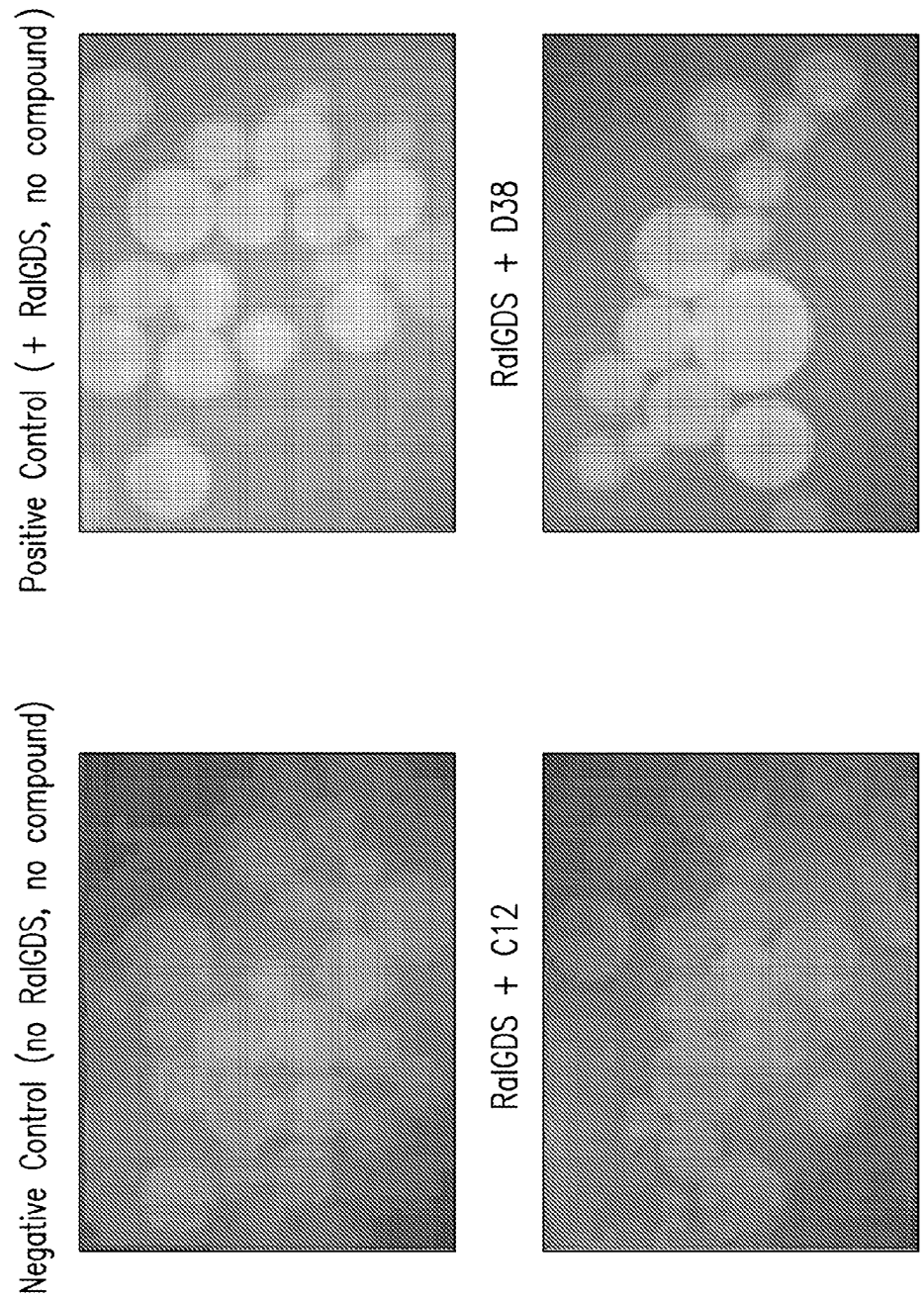
FIG. 13 Disruption of Ras-RalGDS binding with C12 and D38.

Compound B12 was also assayed for its ability to inhibit the PPI between K-Ras and its effector proteins including PI3 kinase, Tiam, and RalGDS. The Myc-tagged effector proteins were immobilized on protein A-beads with an anti-Myc antibody. Addition of Texas red-labeled GST-K-Ras (100 nM) showed binding of K-Ras to beads with immobilized effector proteins. However, addition of 10 µM compound C12 completely blocked by the binding of GST-KRas to each of the three effector proteins. Thus, compound C12 is capable of disrupting the interaction between K-Ras and all four effector proteins that have been tested (Raf, PI3 kinase, Tiam, and RalGDS). An example (Ras-RalGDS interaction) is shown in FIG. 13.

Finally, preliminary cellular assays were performed with compound C12. Singh et al. used RNA interference to down regulate mutant K-RAS in a large number of human cancer cell lines.[102] They reported that the H358 cell line is very sensitive to losing mutant K-Ras whereas the A549 cell line is hardly affected. Both are lung cancer cell lines. Compound C12 was tested against H358 and A549 cells in a MTT assay, which measures proliferation and survival. Consistent with the RNAi study, H358 cells were significantly more sensitive to compound C12 than A549 cells ($IC_{50}$ of ~10 and ~50 µM, respectively) (FIG. 14).

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

F. REFERENCES

1. Pai, E. F., et al. Structure of the guanine-nucleotide-binding domain of the Ha-ras oncogene product p21 in the triphosphate conformation. *Nature* 341, 209-214 (1989).
2. Milburn, M. V., et al. Molecular switch for signal transduction: structural differences between active and inactive forms of protooncogenic ras proteins. *Science* 247, 939-945 (1990).
3. Peattie, D. A., Hsiao, K., Benasutti, M. & Lippke, J. A. Three distinct messenger RNAs can encode the human immunosuppressant-binding protein FKBP. *Gene* 150, 251-257 (1994).
4. Futer, O., DeCenzo, M. T., Aldape, R. A. & Livingston, D. J. FK506 binding protein mutational analysis. Defining the surface residue contributions to stability of the calcineurin co-complex. *Journal of Biological Chemistry* 270, 18935-18940 (1995).
5. Sabatini, D. M., Erdjument-Bromage, H., Lui, M., Tempst, P. & Snyder, S. H. RAFT1: a mammalian protein that binds to FKBP in a rapamycin-dependent fashion and is homologous to yeast TORs. *Cell* 78, 35-43 (1994).
6. Brown, E. J., et al. A mammalian protein targeted by G1-arresting rapamycin-receptor complex. *Nature* 369, 756-758 (1994).
7. Jin, L. & Harrison, S. C. Crystal structure of human calcineurin complexed with cyclosporin A and human cyclophilin. *Proceedings of the National Academy of Sciences of the United States of America* 99, 13522-13526 (2002).
8. Etzkorn, F. A. C., Z. Y.; Stolz, L. A.; Walsh C. T. Cylophilin residues that affect noncompetitive inhibition of the protein serine phosphatase activity of calcineurin by the cyclophilin.cyclosporin A complex. *Biochemistry* 33, 2380-2388 (1994).
9. Zenke, G., et al. Sanglifehrin A, a novel cyclophilin-binding compound showing immunosuppressive activity with a new mechanism of action. *Journal of Immunologyl* 66, 7165-7171 (2001).
10. Wennerberg, K., Rossman, K. L. & Der, C. J. The Ras superfamily at a glance. *Journal of Cell Science* 118, 843-846 (2005).
11. Giehl, K. Oncogenic Ras in tumour progression and metastasis. *Biological Chemistry* 386, 193-205 (2005).
12. Walker, K. & Olson, M. F. Targeting Ras and Rho GTPases as opportunities for cancer therapeutics. *Current Opinion in Genetics & Development* 15, 62-68 (2005).
13. Hingorani, S. R., et al. Preinvasive and invasive ductal pancreatic cancer and its early detection in the mouse. *Cancer Cell* 4, 437-450 (2003).
14. Hingorani, S. R., et al. Trp53R172H and KrasG12D cooperate to promote chromosomal instability and widely metastatic pancreatic ductal adenocarcinoma in mice. [see comment]. *Cancer Cell* 7, 469-483 (2005).
15. Aguirre, A. J., et al. Activated Kras and Ink4a/Arf deficiency cooperate to produce metastatic pancreatic ductal adenocarcinoma. *Genes & Development* 17, 3112-3126 (2003).
16. Singh, A., et al. A gene expression signature associated with "K-Ras addiction" reveals regulators of EMT and tumor cell survival. *Cancer Cell* 15, 489-500 (2009).
17. Sebti, S. M. & Adjei, A. A. Farnesyltransferase inhibitors. *Seminars in Oncology* 31, 28-39 (2004).
18. Holt, D. A., Luengo J. L., Yamashita D., Oh H-J., Konilian A. L., Yen H-K., Rozamus L. W., Brandt M., Bossard M. J., Levy M. A., Eggleston D., Liang J., Schults L. W., Stout T., Clardy J. Design, Synthesis, and Kinetic Evaluation of High-Affinity FKBP Ligands and the X-ray Crystal Structures of Their Complexes with FKBP. *J. Am. Chem. Soc* 115, 9925-9938 (1993).
19. Dubowchik, G. M., Ditta, J. L., Herbst, J. J., Bollini, S. & Vinitsky, A. Fluoresceinated FKBP ligands for a high-throughput fluorescence polarization assay. *Bioorganic & Medicinal Chemistry Letters* 10, 559-562 (2000).
20. Braun, P. D. & Wandless, T. J. Quantitative analyses of bifunctional molecules. *Biochemistry* 43, 5406-5413 (2004).
21. Maynard-Smith, L. A., Chen, L. C., Banaszynski, L. A., Ooi, A. G. & Wandless, T. J. A directed approach for engineering conditional protein stability using biologically silent small molecules. *Journal of Biological Chemistry* 282, 24866-24872 (2007).

22. Harrison, R. K. & Stein, R. L. Substrate specificities of the peptidyl prolyl cis-trans isomerase activities of cyclophilin and FK-506 binding protein: evidence for the existence of a family of distinct enzymes. *Biochemistry* 29, 3813-3816 (1990).
23. Lam, K. S., et al. A new type of synthetic peptide library for identifying ligand-binding activity. [erratum appears in Nature 1992 Dec. 24-31; 360(6406):768]. *Nature* 354, 82-84 (1991).
24. Houghten, R. A., et al. Generation and use of synthetic peptide combinatorial libraries for basic research and drug discovery. *Nature* 354, 84-86 (1991).
25. Thakkar, A., Wavreille, A. S. & Pei, D. Traceless capping agent for peptide sequencing by partial edman degradation and mass spectrometry. *Analytical Chemistry* 78, 5935-5939 (2006).

What is claimed is:

1. A compound comprising (a) a protein binding moiety and (b) an effector region, wherein said protein binding moiety binds to a blocking protein, and wherein said effector region binds to a target protein, and further wherein the protein binding moiety is:

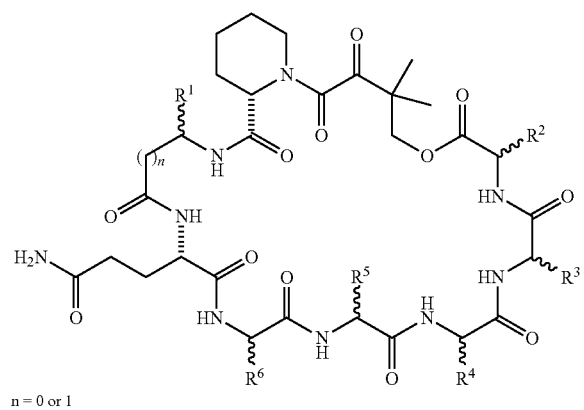

n = 0 or 1 wherein $R^1$ is D-β-homoPhe; $R^2$ is L-Thr; $R^3$ is L-Ala; and $R^4$ is L-Ala.

2. A method of inhibiting a binding event between a target protein and a binding protein, comprising: administering to a cell in vitro an effective amount of the compound of claim 1.

3. The method of claim 2, wherein said blocking protein is FKBP.

4. The method of claim 2, wherein the molecule is a cyclic molecule.

5. The method of claim 2, wherein the target protein is K-Ras.

6. A library comprising a multiplicity of bifunctional inhibitor molecules, each of said molecules comprising (a) a protein binding moiety and (b) an effector region, wherein said protein binding moiety binds to a blocking protein, and wherein said effector region binds to a target protein, and further wherein the protein binding moiety is:

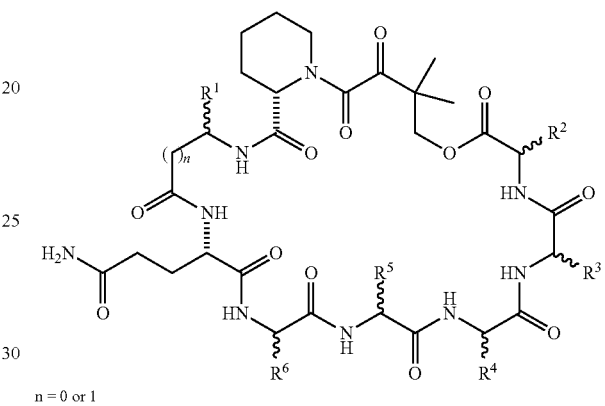

n = 0 or 1 wherein $R^1$ is D-β-homoPhe; $R^2$ is L-Thr; $R^3$ is L-Ala; and $R^4$ is L-Ala.

7. A method of preparing the compound of claim 1, the method comprising the step of covalently bonding the protein binding moiety to the effector region.

8. The method of claim 7, wherein the effector region is generated randomly prior to the bonding step.

9. A method of treating a patient having a disorder comprising the step of administering the compound of claim 1 in an amount effective to treat the disorder in the patient.

* * * * *

UNITED STATES PATENT AND TRADEMARK OFFICE
CERTIFICATE OF CORRECTION

PATENT NO. : 9,260,484 B2
APPLICATION NO. : 14/126343
DATED : February 16, 2016
INVENTOR(S) : Briesewitz et al.

Page 1 of 1

It is certified that error appears in the above-identified patent and that said Letters Patent is hereby corrected as shown below:

In the Specification

Column 1, Lines 17-20 replace the Government Support Clause with:
--This invention was made with government support under grant numbers AI062901, GM062820, and CA132855 awarded by the National Institutes of Health. The government has certain rights in the invention.--

Signed and Sealed this
Fifteenth Day of September, 2020

Andrei Iancu
*Director of the United States Patent and Trademark Office*